(12) United States Patent
Weck

(10) Patent No.: US 11,478,678 B2
(45) Date of Patent: Oct. 25, 2022

(54) POSTURAL PLATFORM TRAINING DEVICE

(71) Applicant: BOSU Fitness, LLC, Wilmington, DE (US)

(72) Inventor: David S. Weck, San Diego, CA (US)

(73) Assignee: BOSU Fitness, LLC, Wilmington, DE (US)

( * ) Notice: Subject to any disclaimer, the term of this patent is extended or adjusted under 35 U.S.C. 154(b) by 43 days.

(21) Appl. No.: 16/913,350

(22) Filed: Jun. 26, 2020

(65) Prior Publication Data

US 2020/0406091 A1 Dec. 31, 2020

Related U.S. Application Data

(60) Provisional application No. 62/867,383, filed on Jun. 27, 2019.

(51) Int. Cl.
*A63B 22/18* (2006.01)
*A61F 5/01* (2006.01)
(Continued)

(52) U.S. Cl.
CPC ............ *A63B 22/18* (2013.01); *A61F 5/0127* (2013.01); *A63B 21/00178* (2013.01);
(Continued)

(58) Field of Classification Search
CPC ......... A63B 22/18; A63B 22/16; A63B 22/14; A63B 23/08–085; A63B 23/04;
(Continued)

(56) References Cited

U.S. PATENT DOCUMENTS 2,518,649 A * 8/1950 Tydings ................. A43B 7/24
36/144
3,297,320 A * 1/1967 Salvatore ............ A63B 23/085
482/79

(Continued)

FOREIGN PATENT DOCUMENTS

WO 0105260 A1 1/2001

OTHER PUBLICATIONS

International Search Report including Written Opinion for PCT/US2020/03988 dated Oct. 13, 2020; 12 pages.

*Primary Examiner* — Garrett K Atkinson
*Assistant Examiner* — Kathleen M Fisk
(74) *Attorney, Agent, or Firm* — Lerner, David, Littenberg, Krumholz & Mentlik, LLP

(57) ABSTRACT

Disclosed herein are devices, systems and methods for redistributing the normal weight distribution of a user in a standing position. One example is a postural platform for either the left or right foot having a bottom surface defining a reference plane, a top surface configured as a foot contact surface and a perimeter side wall between the bottom and top surfaces. The top surface is rotated about a first rotational axis parallel to the reference plane and rotated about a second rotational axis orthogonal to the reference plane. In another example, a system includes first and second postural platforms that are independent of one another. In other (Continued)

examples, the device is a sandal, shoe, sneaker or any foot covering with a tops surface being at a complex angle to a bottom surface.

19 Claims, 13 Drawing Sheets

(51) Int. Cl.
    *A63B 23/04*    (2006.01)
    *A63B 22/14*    (2006.01)
    *A43B 7/24*     (2006.01)
    *A63B 21/00*    (2006.01)
    *A63B 22/00*    (2006.01)
    *A63B 71/06*    (2006.01)

(52) U.S. Cl.
    CPC .............. *A63B 23/04* (2013.01); *A43B 7/24* (2013.01); *A63B 22/14* (2013.01); *A63B 2022/0038* (2013.01); *A63B 2023/0411* (2013.01); *A63B 2071/0694* (2013.01); *A63B 2208/0204* (2013.01); *A63B 2220/52* (2013.01)

(58) Field of Classification Search
    CPC . A63B 23/0458; A63B 23/0464; A63B 23/10; A63B 26/003; A63B 21/00178; A63B 21/4011–4015; A63B 21/4047–4049; A63B 21/4034; A63B 21/072; A63B 21/00047; A63B 21/4039; A63B 21/4037; A63B 2220/52; A63B 2023/0411; A63B 2208/0204; A63B 2071/0694; A63B 2071/0655; A63B 2071/0625; A63B 2022/0038; A63B 71/00; A63B 71/0622; A43B 7/24; A61F 5/0127; A61F 5/0111; A61G 13/125; A61G 13/126; A47C 16/00; A47C 16/02; A47C 16/025
    USPC ........................................................ 128/845
    See application file for complete search history.

(56) References Cited

U.S. PATENT DOCUMENTS

| | | | | |
|---|---|---|---|---|
| 3,990,159 | A | * | 11/1976 | Borgeas .................. A43B 7/28 36/28 |
| 4,253,661 | A | * | 3/1981 | Russell ............ A63B 21/00047 482/51 |
| 4,297,797 | A | | 11/1981 | Meyers |
| 4,642,911 | A | | 2/1987 | Talarico, II |
| 4,917,385 | A | * | 4/1990 | Brown ............... A63B 69/3667 473/273 |
| 4,934,073 | A | | 6/1990 | Robinson |
| 5,263,863 | A | * | 11/1993 | Stefani ............... A63B 69/3673 473/272 |
| 5,491,912 | A | | 2/1996 | Snabb et al. |
| 5,566,478 | A | * | 10/1996 | Forrester .............. A43B 3/0042 36/126 |
| 5,656,000 | A | * | 8/1997 | Russell .............. A63B 69/0035 482/52 |
| 5,799,659 | A | * | 9/1998 | Stano .................... A61F 5/0111 128/882 |
| 5,810,673 | A | * | 9/1998 | Castleberry ........ A63B 69/3673 473/217 |
| 6,315,695 | B1 | * | 11/2001 | Follett .................... A63B 22/16 482/79 |
| D491,246 | S | * | 6/2004 | Walsh .......................... D21/791 |
| 7,169,098 | B1 | * | 1/2007 | McGanty ............. A61H 1/0237 482/146 |
| 7,294,114 | B1 | | 11/2007 | Clement et al. |
| D557,366 | S | * | 12/2007 | Witt ............................. D21/791 |
| 10,085,868 | B2 | * | 10/2018 | Kitano ............... A63B 21/4025 |
| 10,271,611 | B2 | * | 4/2019 | Adair ................... A43B 13/143 |
| 10,960,260 | B1 | * | 3/2021 | Weber .................... A63B 23/04 |
| 2009/0181811 | A1 | * | 7/2009 | Bard .................. A63B 69/0002 473/452 |
| 2010/0267498 | A1 | * | 10/2010 | Bard .................. A63B 69/0002 473/452 |
| 2012/0040810 | A1 | * | 2/2012 | Astilla ............... A63B 21/0023 482/131 |
| 2017/0224048 | A1 | * | 8/2017 | Nagano .................. A43B 7/141 |
| 2020/0324164 | A1 | * | 10/2020 | Amis ..................... A63B 23/10 |

* cited by examiner

POSTURAL PLATFORM TRAINING DEVICE

CROSS-REFERENCE TO RELATED APPLICATIONS

This application claims the benefit of the filing date of U.S. Provisional Patent Application No. 62/867,383 filed Jun. 27, 2019, the disclosure of which is hereby incorporated herein by reference.

BACKGROUND OF THE INVENTION

When standing upright, a person balances his or her body over their feet. Generally, the spine should be aligned over the pelvis, with the weight of the body evenly distributed between the left and right feet. Many people stand with more weight over one foot or with their weight over only part of their feet.

The bones of the leg and foot form part of the appendicular skeleton that supports the many muscles of the lower limbs. These muscles work together to produce movements such as standing, walking, running and jumping. At the same time, the bones and joints of the leg and foot must be strong enough to support the weight of the body while remaining flexible enough for movement and balance.

In the lower leg, the tibia bears most of the weight of the body while the fibula supports the muscles of balance in the lower leg and ankle. The tibia forms the flexible ankle joint with the tarsal bones of the foot. Body weight is distributed among the seven tarsals, which can shift slightly to provide minute adjustments to the position of the ankle and foot. The calcaneus, or heel bone, is the largest tarsal bone and rests on the ground when the body is standing.

The tarsal bones and the five long metatarsal bones together form the arches of the foot. Body weight supported by the foot is spread across the arches from the tarsal and metatarsal bones, which make contact with the ground while standing. Like the tarsal bones, the position of the metatarsals can be adjusted to change the shape of the foot and affect balance and posture of the body.

SUMMARY OF THE INVENTION

Given that weight distribution of the body while standing is generally directed medially or toward the inside of the body, a postural platform having a foot contact surface angled with respect to the planes of the body and a plane of the ground can redistribute body weight laterally and toward substantial support of skeletal bones.

In one aspect, a training device is provided that includes a first portion having a substantially planar first foot contact surface disposed at a substantially 11.25° tilt relative to a reference ground plane, and a second portion having a substantially planar second foot contact surface disposed at a substantially 11.25° tilt relative to the ground plane and turned substantially 45° from the first contact surface relative to the ground plane.

In another aspect, a training device is provided that includes a housing comprising a bottom surface and a top surface, where the housing is configured to orient the top surface relative to a ground plane, wherein the ground plane is a plane orthogonal to the direction of gravity, and where the top surface is substantially co-planar with a top surface plane, wherein the top surface plane is disposed at a first angle relative to the ground plane. The training device may also include indicia for conveying a location at which the placement of the sole of a foot on the top surface causes the longitudinal axis of the foot to be substantially parallel with an alignment reference line, wherein: the alignment reference line comprises the intersection line of the top surface plane with an alignment reference plane; the alignment reference plane is orthogonal to the ground plane and disposed at a second angle relative to another reference plane; and said another plane is orthogonal to the ground plane and contains the line at which the top surface plane intersects the ground plane.

One aspect is a postural platform to redistribute weight of a user in a standing position. The postural platform includes a bottom surface defining a reference plane, a top surface configured as a contact surface for a foot of the user, and a perimeter side wall between the bottom and top surfaces. The top surface is rotated about a first rotational axis parallel to the reference plane and is rotated about a second rotational axis orthogonal to the reference plane. When the foot of the user is in contact with the top surface of the postural platform, a first point of contact on the top surface corresponding to an inside of a ball of the foot is higher with respect to the reference plane than a second point of contact corresponding with an inside of a heel of the foot, the second point of contact being higher with respect to the reference plane than a third point of contact corresponding with an outside of the ball of the foot, the third point of contact being higher with respect to the reference plane than a fourth point of contact corresponding with an outside of the heel of the foot.

In one embodiment of this aspect, the top surface substantially conforms to the shape of the foot of the user. In another embodiment, the top surface is substantially planar.

In one embodiment of this aspect, the top surface is rotated between 10° and 12.5° about the first rotational axis and top surface is rotated between 20° and 25° about the second rotational axis.

In another embodiment, the top surface has an outer periphery shaped to substantially match an outer periphery of a foot of a user.

In yet another embodiment, the top surface includes visual indicia defining how a foot of a user is to be oriented relative to the top surface when the foot of the user is in contact with the top surface.

In still yet another embodiment, the postural platform further includes a pivot member coupled to the bottom surface of the postural platform. The pivot member allows the top surface to rotate about the second rotational axis. The pivot member has a top plate that is fixedly coupled to the bottom surface of the performance platform and a bottom plate that rotates with respect to the top plate along the second rotational axis.

In another aspect, a postural platform to redistribute weight of a user in a standing position includes a bottom surface defining a reference plane, a top surface configured as a contact surface for a foot of the user, the top surface having a complex angle with respect to the bottom surface such that when the foot of the user is in contact with the top surface, a first point of contact on the top surface corresponding to an inside of a ball of the foot is higher with respect to the reference plane than a second point of contact corresponding with an inside of a heel of the foot, the second point of contact being higher with respect to the reference plane than a third point of contact corresponding with an outside of the ball of the foot, the third point of contact being higher with respect to the reference plane than a fourth point of contact corresponding with an outside of the heel of the foot, a perimeter side wall between the bottom and top surfaces, and a covering coupled to at least a portion of a perimeter of the top surface for forming at least a partial housing for the foot of the user located between the top surface and covering.

In one embodiment of this aspect, the top surface is substantially planar. In another embodiment, the top surface substantially conforms to a natural shape of the foot of the user.

In one embodiment, the complex angle between the top and bottom surfaces is defined by the top surface is rotated between 10° and 12.5° about a first rotational axis parallel to the reference plane and rotated between 20° and 25° about the second rotational axis orthogonal to the reference plane.

In another embodiment of this aspect, the top surface includes visual indicia defining how the foot of the user is to be oriented relative to the top surface when the foot of the user is in contact with the top surface.

In yet another embodiment of this aspect, the postural platform further includes a pivot member coupled to the bottom surface of the postural platform, the pivot member configured to allow the foot contact surface to rotate about a second rotational axis orthogonal to the reference plane. The pivot member has a top plate that is fixedly coupled to the bottom surface of the postural platform and a bottom plate that rotates with respect to the top plate along the second rotational axis.

In another aspect, a postural platform system designed to redistribute weight of a user in a standing position includes a left foot platform having a bottom surface defining a reference plane, a top surface configured to support a left foot of the user, the top surface being rotated downwardly in a first direction about a first rotational axis parallel to the reference plane and rotated counter-clockwise about a second rotational axis orthogonal to the reference plane, and a right foot platform having a bottom surface defining a reference plane, a top surface configured to support a right foot of the user, the top surface being rotated downwardly in a second direction opposite the first direction about the first rotational axis parallel to the reference plane and rotated clockwise about the second rotational axis orthogonal to the reference plane.

In one embodiment, each of the left foot and right foot platforms have a covering coupled to at least a portion of a perimeter of the respective top surfaces of each of the platforms for forming at least a partial housing for the respective left and right feet of the user when located between the respective top surfaces and coverings.

DETAILED DESCRIPTION

A training device is disclosed that disposes one or more portions of a person's body at particular angles when a person stands on or is otherwise supported by the device. By way of example, as shown in FIGS. 1-5, the device may have include a left portion with a top surface for contacting the left foot that is rotated substantially 22.5° counter-clockwise and tilted substantially 11.25° downward to the left relative to the forward direction of the device and a right portion with a top surface for contacting the right foot that is rotated substantially 22.5° clockwise and tilted substantially 11.25° downward to the right relative to the forward direction. FIGS. 6-9 provide other views of the device.

Figure 10:
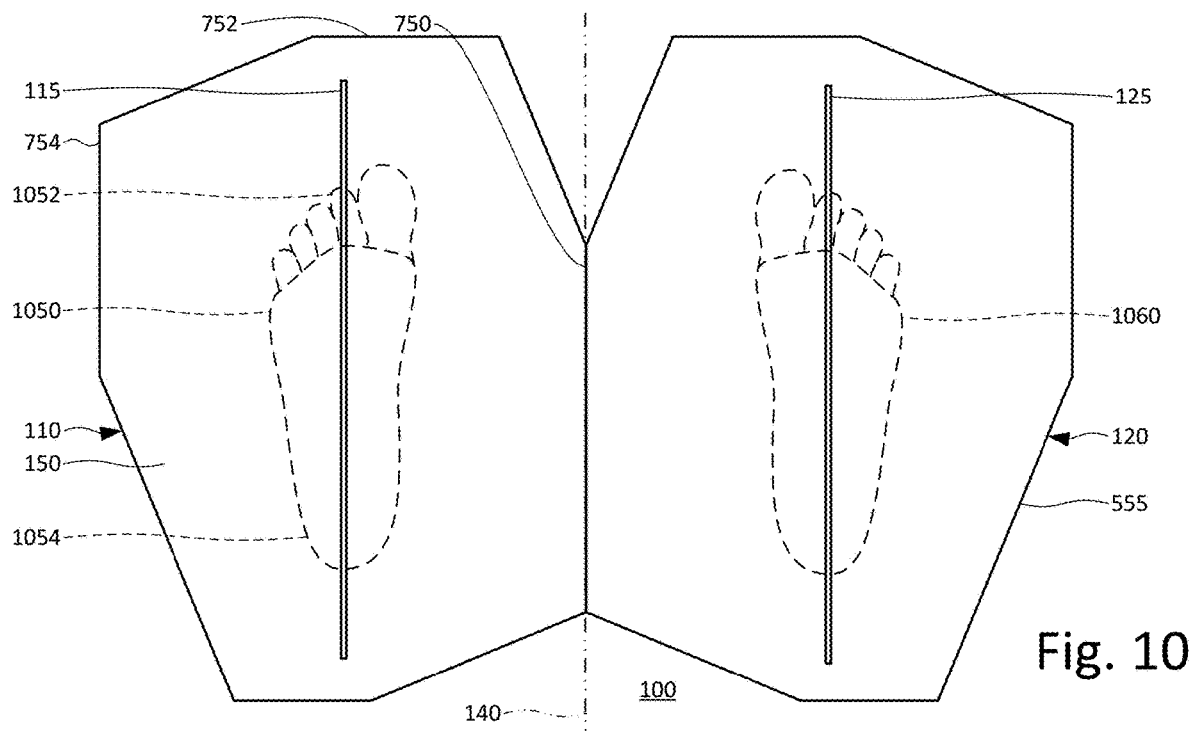
FIG. 10 is a top-down view of the example device shown in FIG. 1.
Figure 11:
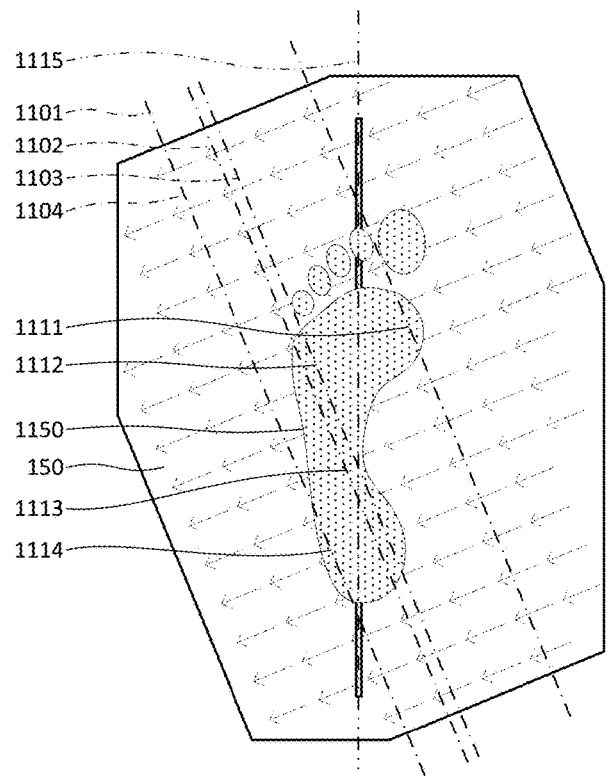
FIG. 11 is a top-down view showing certain features of the left portion of the example device shown in FIG. 1.
Figure 12:
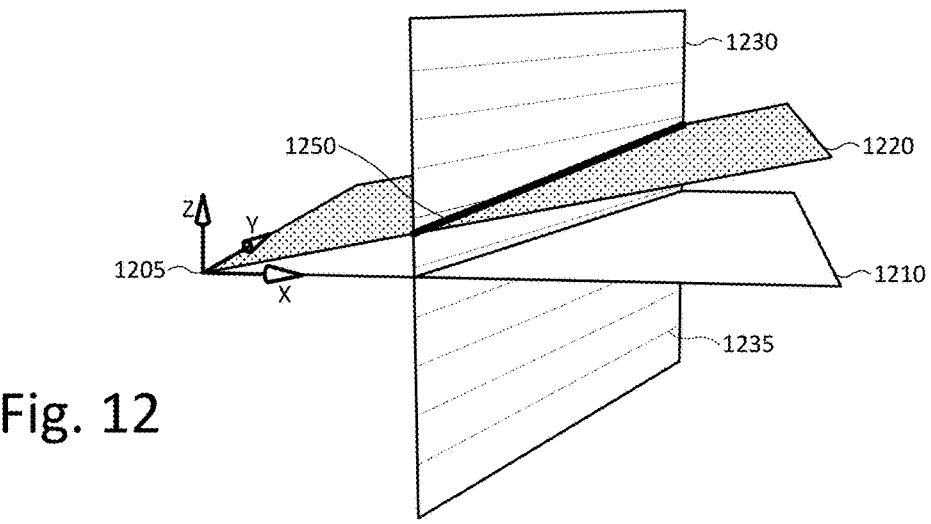
FIG. 12 is a perspective view of reference planes in accordance with the technology disclosed herein.
Figure 13:
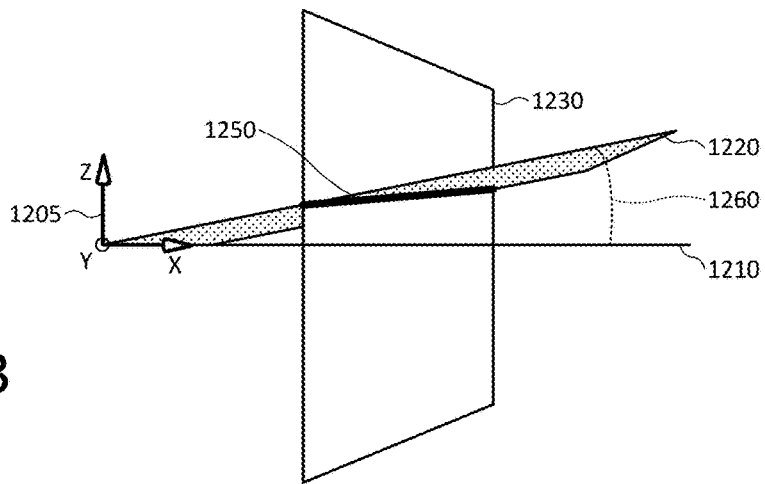
FIG. 13 is a front view of the reference planes shown in FIG. 12.
Figure 14:
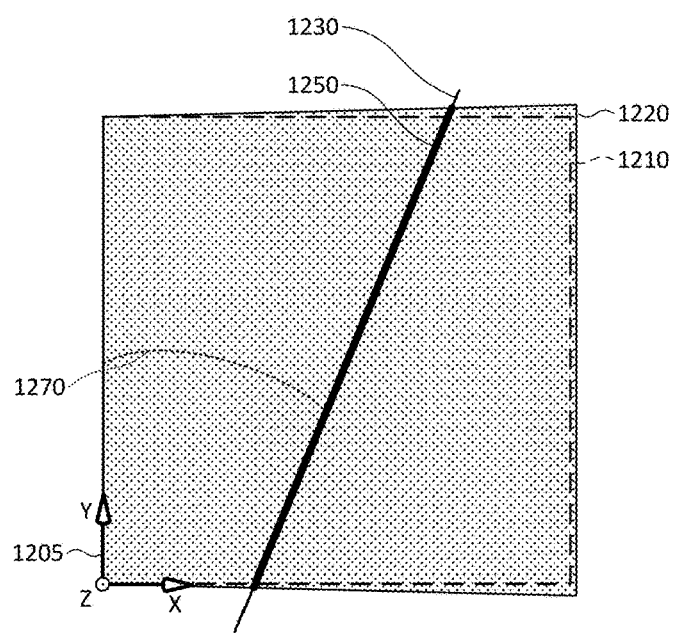
FIG. 14 is a top-down view of the reference planes shown in FIG. 12.

The device may also include indicia instructing how a user may orient his or her body relative to the device. For instance and as shown in FIG. 10-11, the device may include visual indicia that suggests where a person should place one or more of his or her feet on the device. FIGS. 12-14 describe how the indicia may be determined based on the angles of three reference planes associated with, respectively, the bottom surface of the device (which may rest upon the ground surface), the top surface of the device (e.g., the surface upon which a user may rest his or her feet) and how the user may align his or her foot on the top surface.

Figure 15:
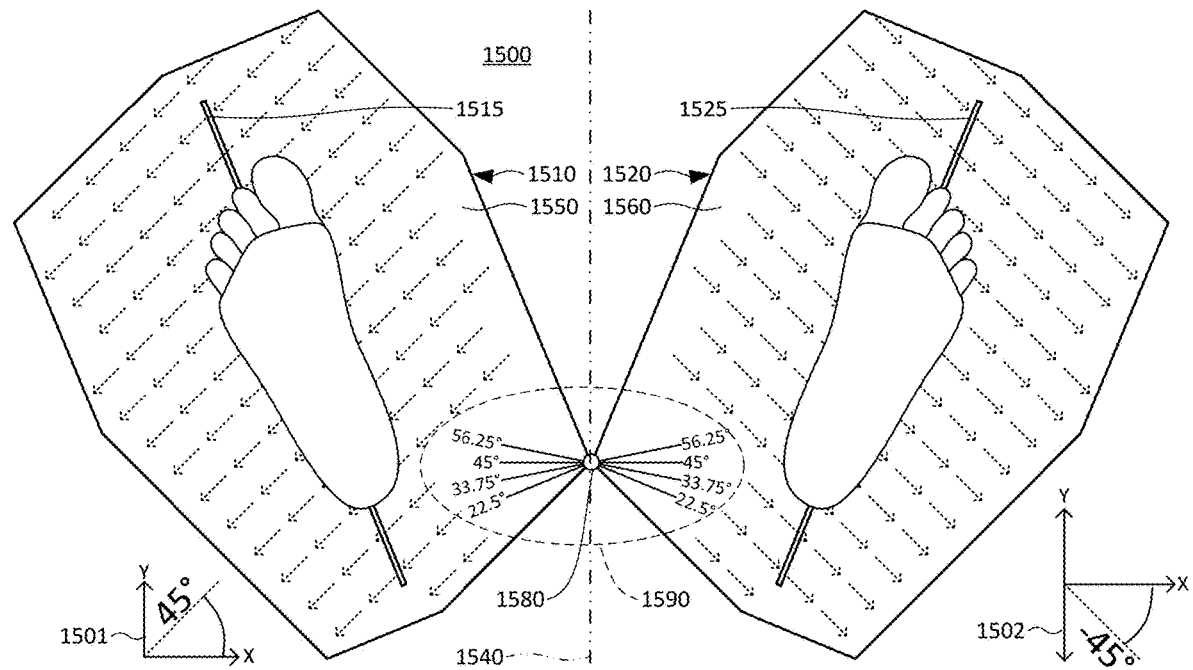
FIG. 15 is a top-down view of an example device in accordance with the technology disclosed herein.
Figure 16:
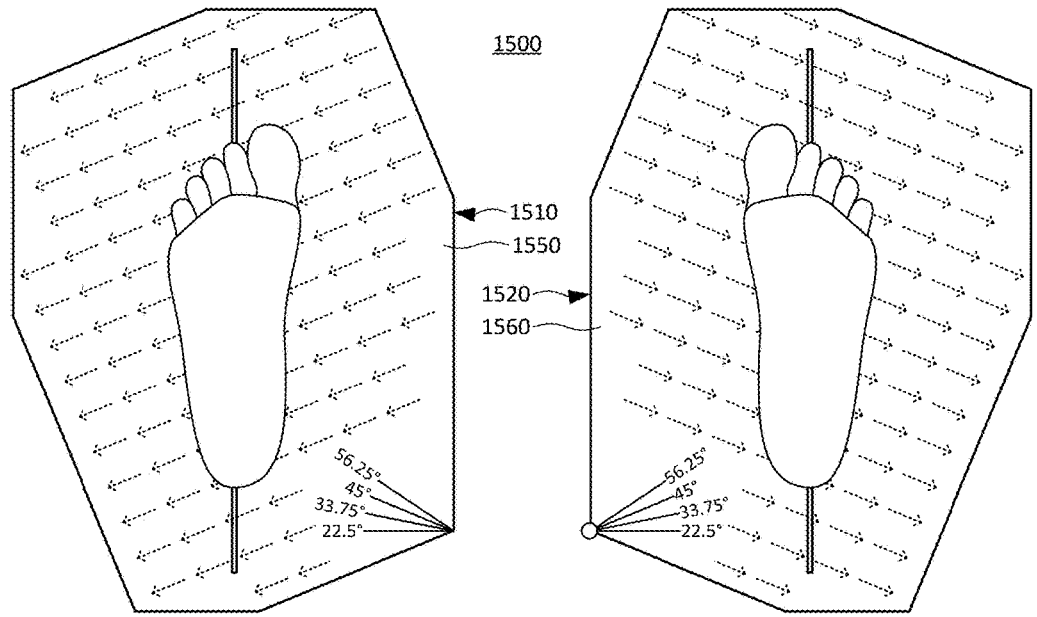
FIG. 16 is a top-down view of another arrangement of the example device shown in FIG. 15.
Figure 17:
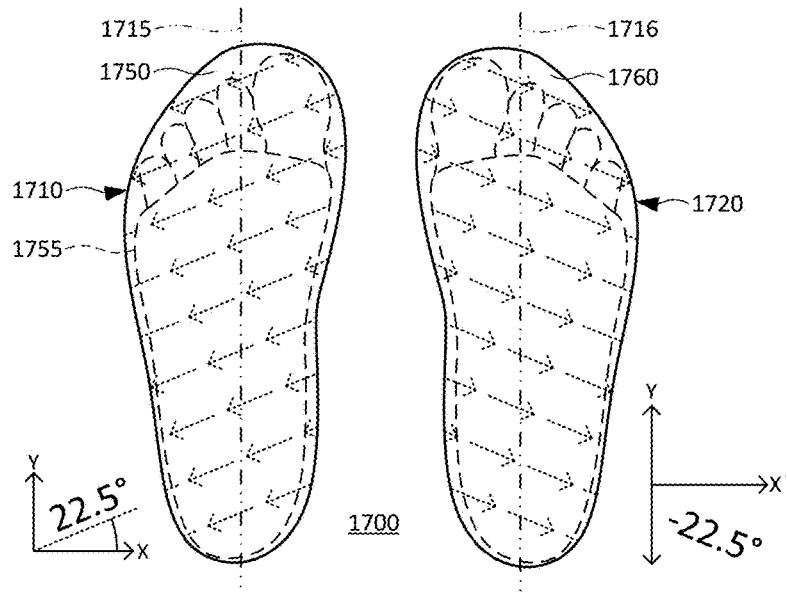
FIG. 17 is a top-down view of the top surface of the sole of a shoe in in accordance the technology disclosed herein.
Figure 18:
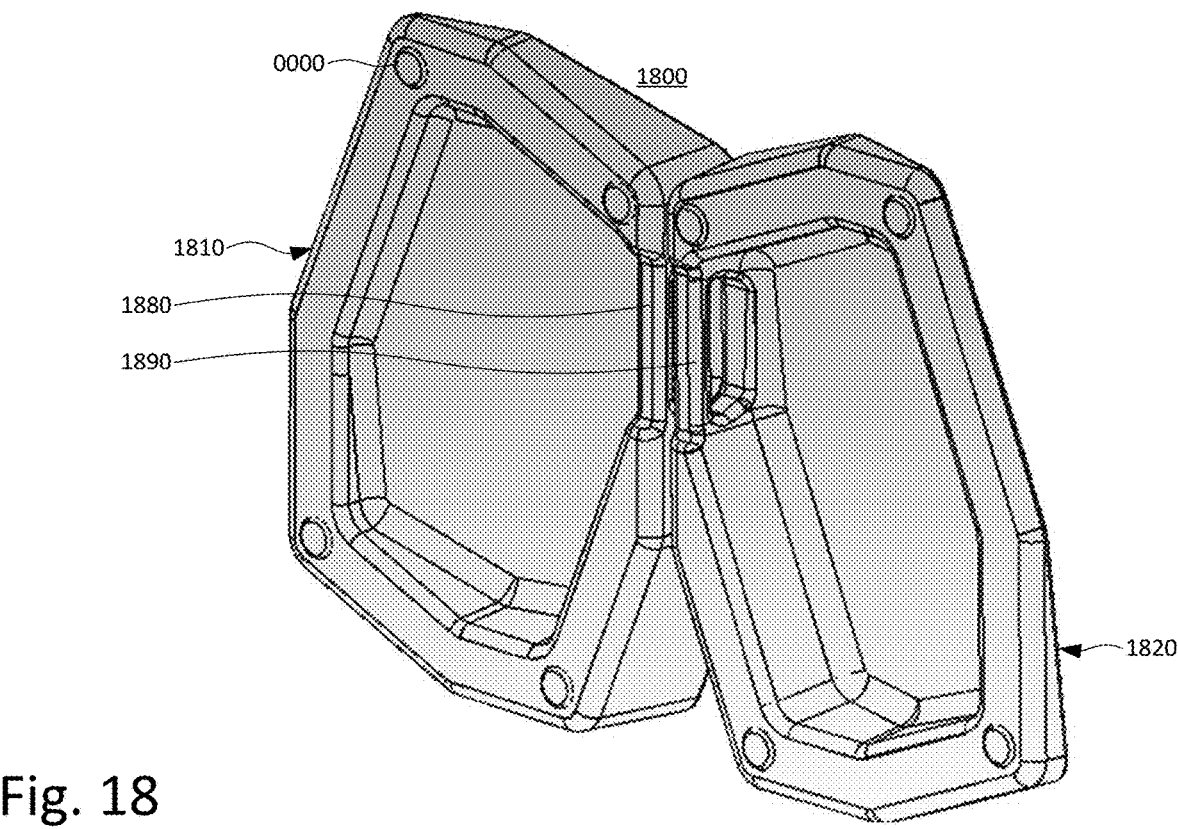
FIG. 18 is a perspective view of the bottom surface of the housing or an example device in accordance with the technology disclosed herein.

FIGS. 15-18 illustrate other examples of the technology disclosed herein. By way of example, FIGS. 15 and 16 illustrate an example wherein the left and right portions are detachably connected to one another at a hinge. FIG. 17 illustrates how a pair of shoes may use the technology and FIG. 18 illustrates how the bottom surface of the device may be arranged.

For ease of reference and understanding, certain elements of the technology disclosed herein may be described relative to a three-dimensional Cartesian coordinate system. In that regard, and as shown by way of example by reference axes 105 in FIG. 1, the three-dimensional coordinate system includes an x-axis, a y-axis orthogonal to the x-axis and intersecting the x-axis at an origin point, and a z-axis that intersects the origin point and is orthogonal to both the x-axis and the z-axis. The x-y plane is defined by the plane containing both the x-axis and the y-axis, the y-z plane is defined by the plane containing both the y-axis and z-axis, and x-z plane is defined by the plane containing both the x-axis and the z-axis. Solely for ease of reference, various examples below assume that the z-axis corresponds with the direction of gravity and the x-y plane generally corresponds with the ground plane, e.g., the plane that is orthogonal to the direction of gravity at the geographic location at which the device is used. However, except where expressly indicated, references herein to an element extending in one direction does not preclude the possibility that the element extends at least in some part in another direction as well.

Figure 1:
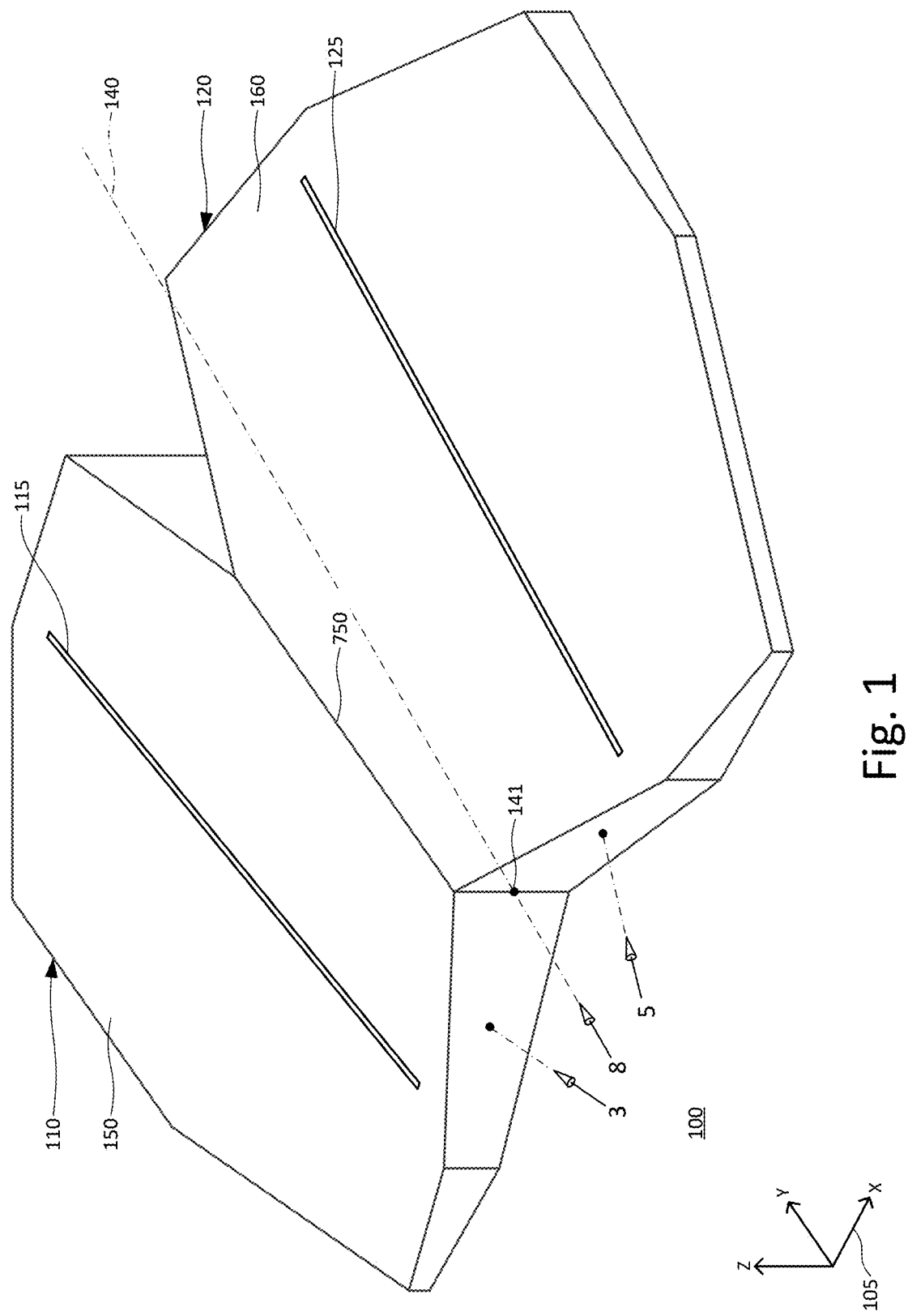
FIG. 1 is an axonometric perspective view of an example device in accordance with the technology disclosed herein.

Device 100 shown in FIG. 1 provides one example of a device in accordance with the technology described herein. The conical arrows of lines of sight 3, 5 and 8 correspond with the views shown in FIGS. 3, 5 and 8 respectively. The lines of sight in FIG. 1 and other figures are shown for reference purposes only.

The device may include a housing with a top surface and bottom surface. For instance, the housing of device 100 may form a left portion 110 and a right portion 120. Left portion 110 includes left top surface 150 and right portion 120 includes right top surface 160. While left top surface 150, right top surface 160 and the bottom surface (not shown in FIG. 1) of the specific example shown in FIG. 1 may feel flat when used by a user, the top and bottom surfaces in accordance with other aspects of the technology described herein may not be. Left top surface 150 and right top surface 160 also include left visual indicia 115 and right visual indicia 125, respectively, which are used to help a user align his or her feet when standing on the device.

For further ease of reference, a device in accordance with the technology disclosed herein may be associated with a forward direction. For instance, device 100 may be associated with a longitudinal axis 140 that stretches in a forward direction from point 141 near the front of device 100 to a point near the back of the device (not shown). For ease of reference, longitudinal axis 140 of device 100 shall be considered parallel to the y-axis of reference axes 105. For further ease of reference, the forward direction may be considered to correspond with the forward direction of the human body.

Figure 2:
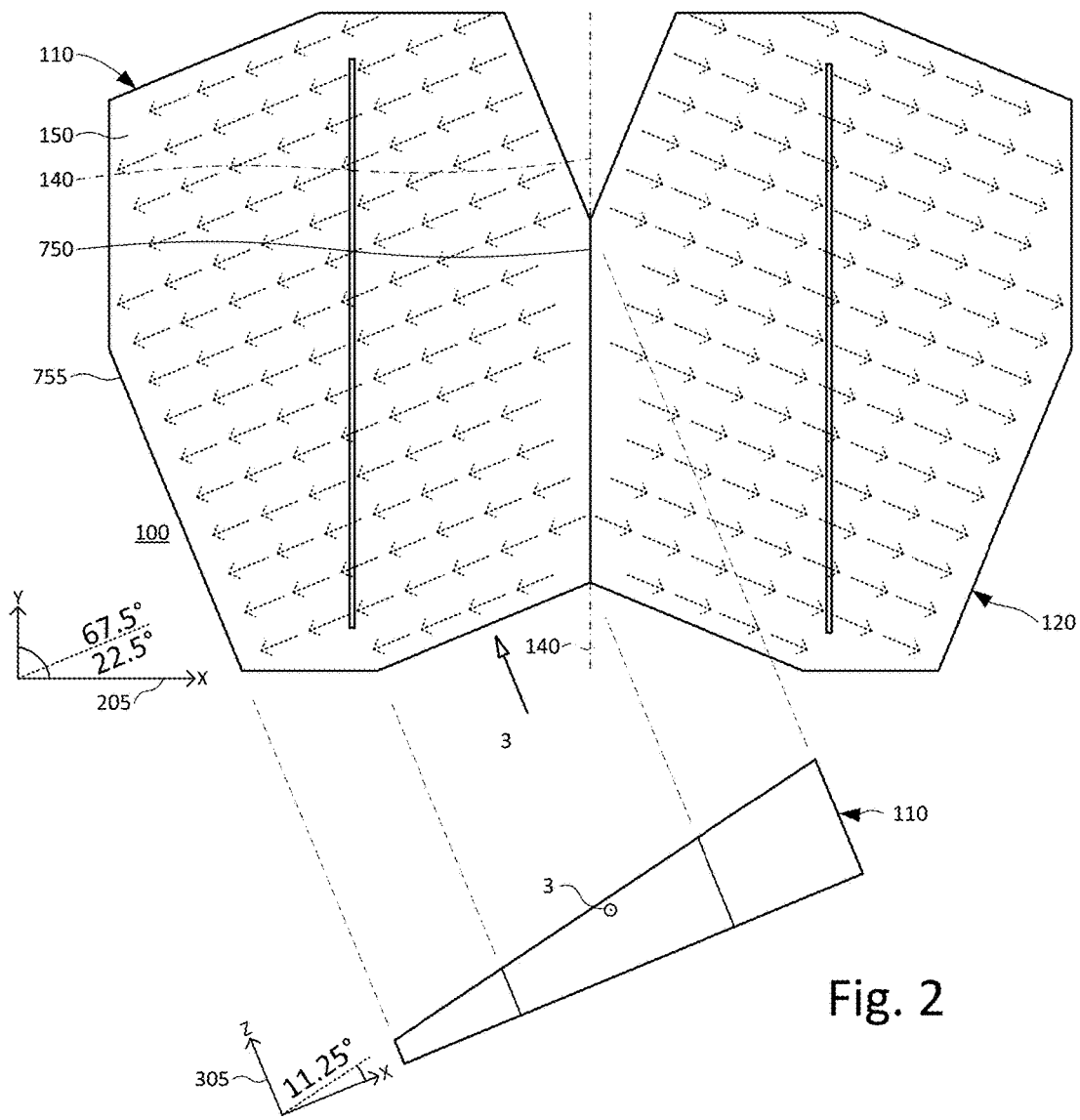
FIG. 2 is a top-down view, and a side view of the left portion, showing certain angles associated with the example device shown in FIG. 1.
Figure 3:
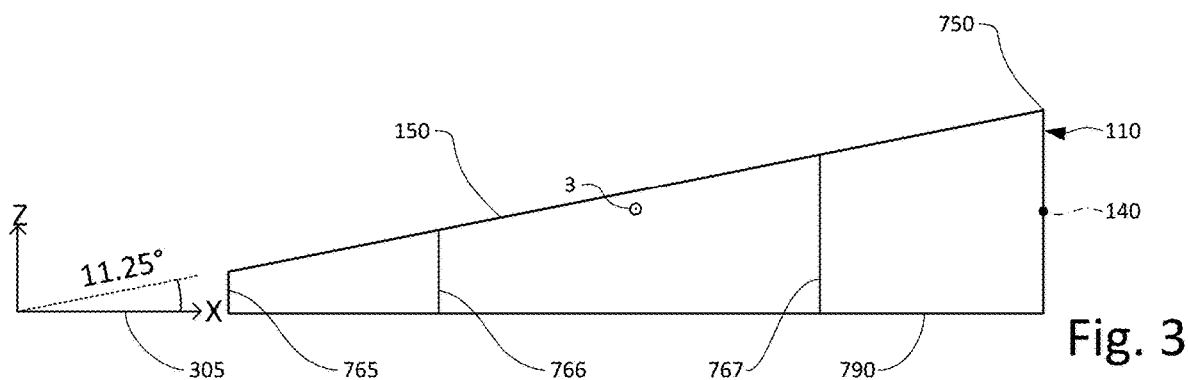
FIG. 3 is a side view of the example device shown in FIG. 1.
Figure 4:
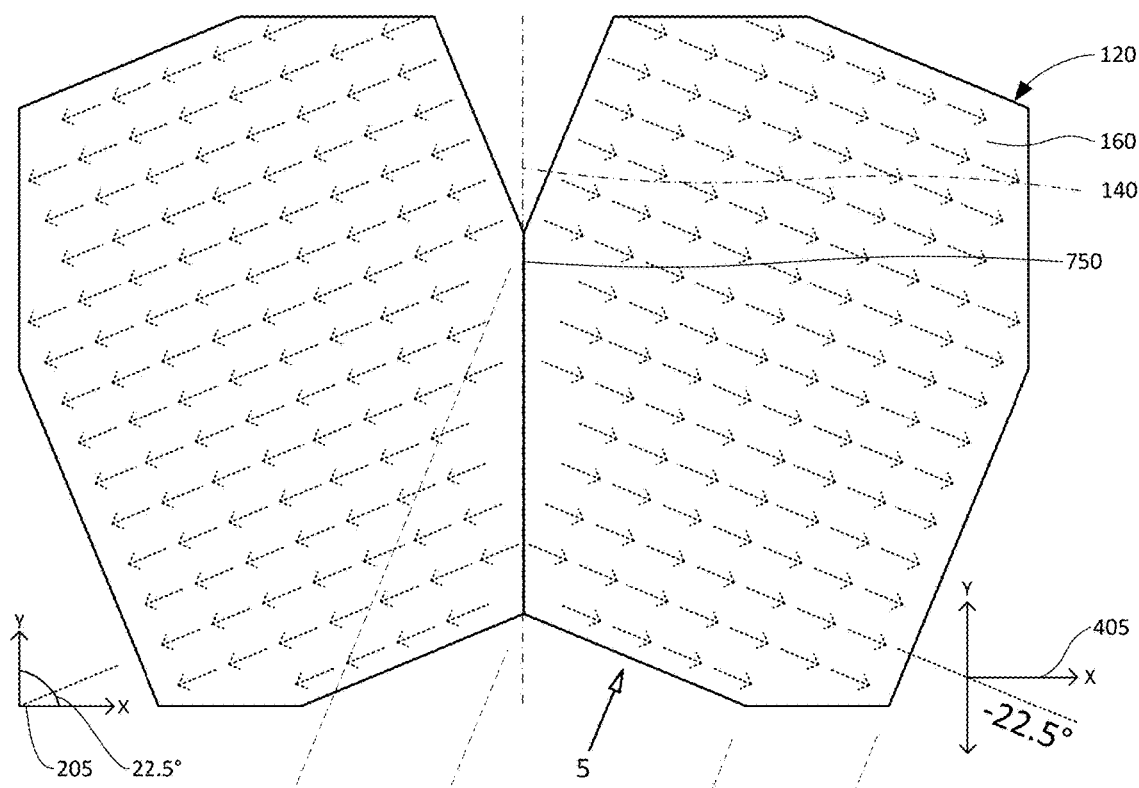
FIG. 4 is a top-down view, and a side view of the right portion, showing certain angles associated with the example device shown in FIG. 1.

As shown in FIGS. 2-5, the device may have a left top surface and a right top surface that are generally disposed at different angles with respect to each other. For example, left top surface 150 and right top surface 160 of the device may be tilted and rotated relative to each other. By further way of example, the orientation of the left top and right top surfaces may be described with respect to longitudinal axis 140. FIGS. 2 and 4 both show a top-down view of device 100. FIG. 2 also shows a front/side view of left portion 110 from the perspective of line of sight 3 as if right portion 120 was removed from device 100, and that same front/side view is reproduced in FIG. 3. FIG. 4 is similar to FIG. 2 in that it shows a top-down view of device 100, but it also shows a front/side view of right portion 120 from the perspective of line of sight 5 as if left portion 110 was removed from device 100. The same front/side view in FIG. 4 is reproduced in FIG. 5.

The bottom surface of the device may be substantially flat. For example and as shown in particular FIGS. 3 and 5, the bottom surface 790 of left portion 110 may be flat and parallel to the x-y plane.

The top surface of the left portion may be tilted downward relative to the center of the device. For example, the dotted arrows in FIG. 2 and other figures indicate the downward tilt direction of the top surface of the device. In that regard, and as shown by axes 205 and axes 305 in FIGS. 2 and 3, respectively, left top surface 150 may be tilted downward and to the left relative to longitudinal axis 140. The tilt may be such that the acute angle between the plane defined by left top surface 150 and the plane generally defined by bottom surface 790 (e.g., the x-y plane generally corresponding with the ground plane) is substantially 11.25° (e.g., 11 to 11.5°) and the left side of left top surface 150 (e.g., near left side edge 755) is lower than the right side of left top surface 150 (e.g., near top center edge 750).

The tilted top surface may also be rotated relative to the center of the device, e.g., rotated in a direction parallel to the bottom surface and a certain number of degrees relative to the device's longitudinal axis. In that regard and as shown relative to axes 205 in FIG. 2, the tilt direction of left top surface 150 is substantially 67.5° counter-clockwise (e.g., 67 to 68°) relative to longitudinal axis 140 in the x-y plane. In other words, the tilt direction of left top surface 150 is rotated substantially 22.5° counter-clockwise compared to what the tilt direction would have been if it was tilted perpendicular to and away from longitudinal axis 140.

Figure 5:
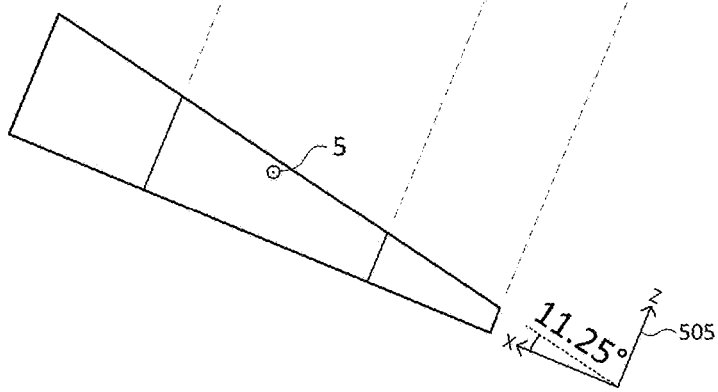
FIG. 5 is a side view of the example device shown in FIG. 1.
Figure 5:
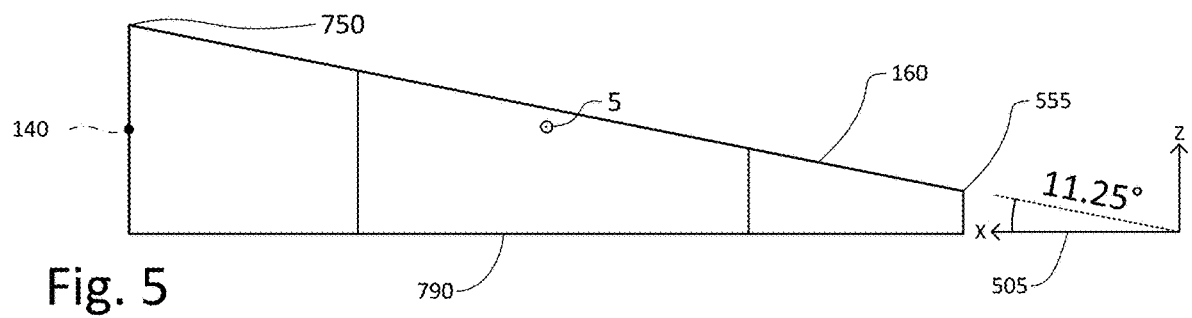

The right top surface may be tilted and rotated in opposite directions to the left top surface. For instance and as shown in FIGS. 4 and 5, right top surface 160 of right portion 120 may be rotated clockwise and tilted downward to the right relative to longitudinal axis 140. By way of example and as shown by axes 405 and axes 505: the acute angle between the plane defined by right top surface 160 and the plane defined by bottom surface 790 may be substantially 11.25°; the right side of right top surface 150 (e.g., near right side edge 555) may be lower than the left side of right top surface 160 (e.g., near top center edge 750); and the tilt direction of right top surface 160 may be rotated substantially −22.5° (e.g., clockwise) compared to what the tilt direction would have been if it was tilted perpendicular to and away from longitudinal axis 140. In that regard the direction of tile of right portion 120 may be turned 45° relative to the angle of tilt of the first portion.

Figure 6:
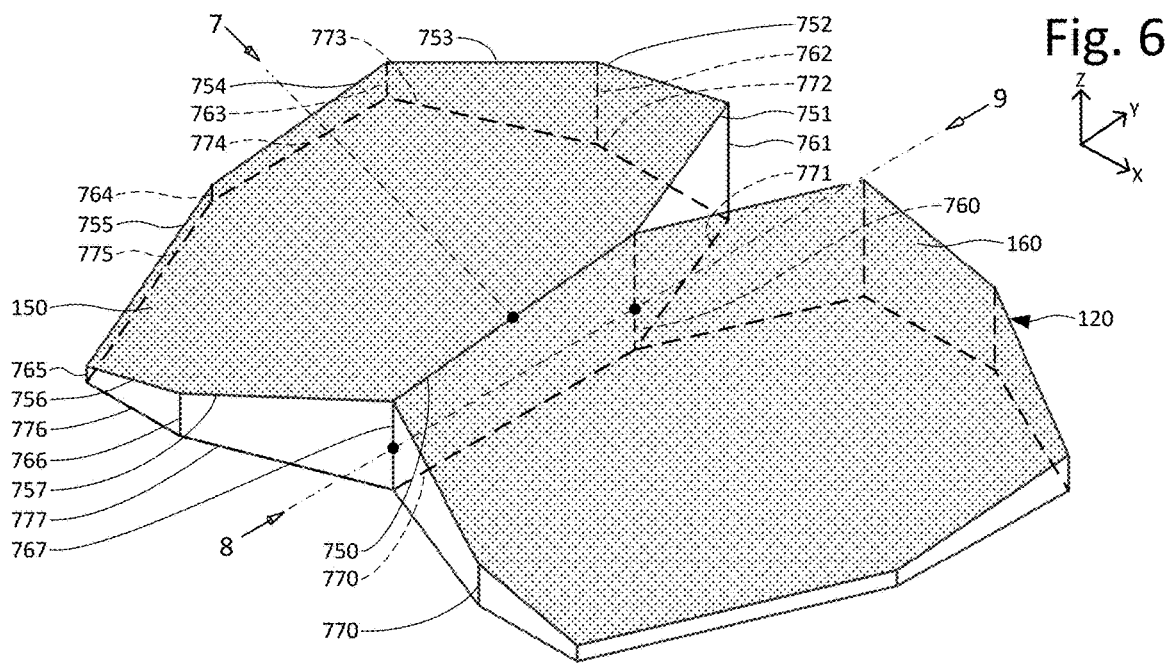
FIG. 6 is an axonometric perspective view of the example device shown in FIG. 1.
Figure 7:
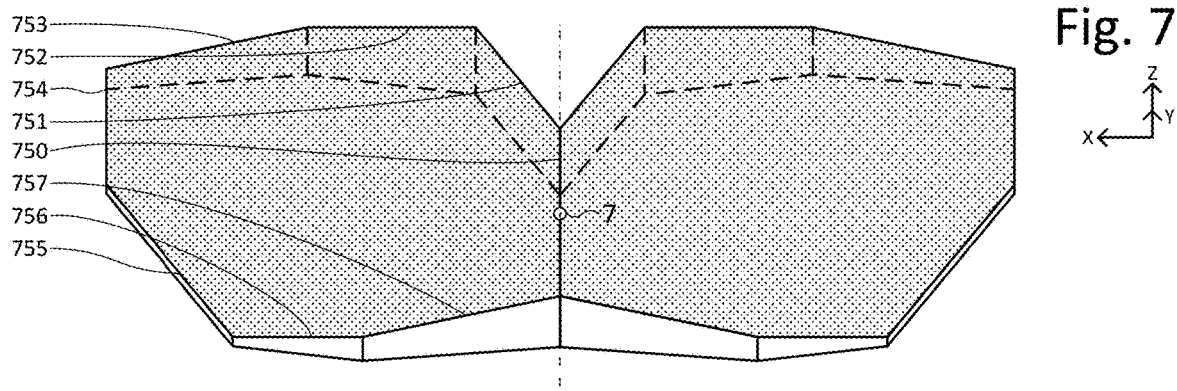
FIG. 7 is a top-down oblique front view of the example device shown in FIG. 1.
Figure 8:
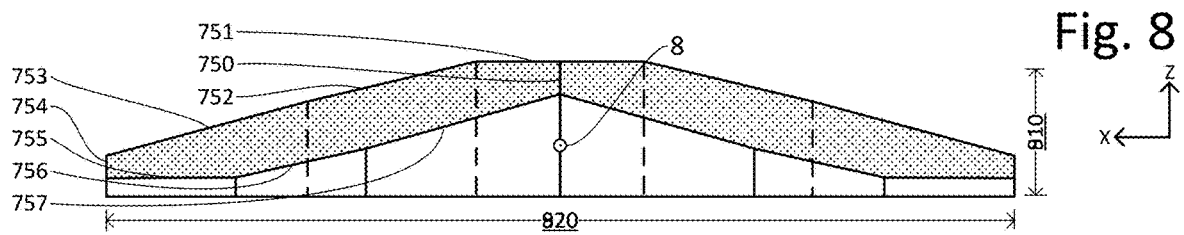
FIG. 8 is a front view of the example device shown in FIG. 1.
Figure 9:
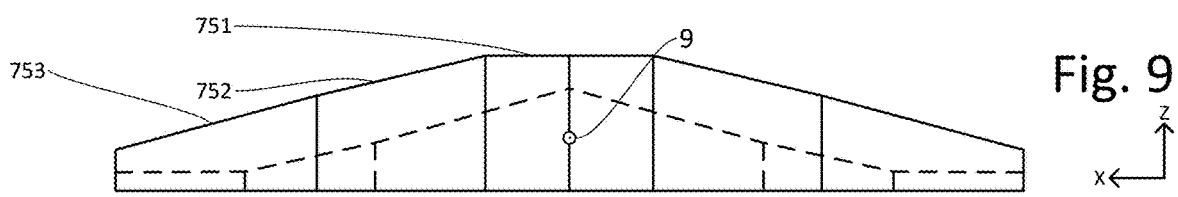
FIG. 9 is a back view of the example device shown in FIG. 1.

FIGS. 6-9 provide additional views of device 100. FIG. 6 provides the same perspective view of device 100 as of FIG. 1. However, unlike FIG. 1, FIG. 6 shades left top surface 150 and right top surface 160, includes dashed lines indicating the presence of hidden edges, and omits left visual indicia 115 and right visual indicia 125. FIG. 6 also includes lines of sight 7 and 9, which correspond with the views shown in FIGS. 7 and 9, respectively. FIG. 7 is a top-down oblique view of device 100, FIG. 8 is a front view of device 100, and FIG. 9 is a back view of device 100.

A device in accordance with the technology disclosed herein may provide indicia for indicating a suggested alignment of a person's body during use. In that regard, device 100 may include indicia indicating how a user should orient his or her feet when standing upon, squatting upon, or is otherwise supported by the device. For instance, left portion 110 may include left visual indicia 115 and right portion 120 may include right visual indicia 125. By way of example, left visual indicia 115 may be a line that is painted on left top surface 150, that is centered between left outer edge 754 and top center edge 750, and that extends in the forward direction, parallel to longitudinal axis 140. Similarly, right visual indicia 125 may be a line that is painted on right top surface 160, is centered between top center edge 750 and right edge 555, and extends in the forward direction, parallel to longitudinal axis 140.

The suggested alignment of a user's feet includes resting each foot on the top surface of the device so each foot points in the forward direction. A user may similarly place the second innermost toe and center of the heel of the user's right foot above right visual indicia 125. In that regard and as shown in FIG. 10, a user may place his or her left foot 1050 on left top surface 150 such that both the second innermost toe 1052 (the toe next to the big toe) and the center of his or her heel 1054 is directly above left foot indicia 115. The visual indicia may also be arranged to enable a user to locate his or her foot in the recommended alignment by aligning the inside heel region of his or her foot slightly wider than the inside ball of the foot region of his or her foot.

The feet indicia may include other mechanisms for indicating a suggested alignment of the feet. For instance, instead of being a painted line, the feet indicia may be a groove embedded in the top of the surface, a footprint embedded in the surface (e.g., similar to the footprint shown in dashed lines in FIG. 10), or any other visual indicia. In addition to or instead of visual indicia, the indicia may comprise other modes of placement detection and feedback that are capable of being perceived by a typical user. By way of example, left top surface 150 and right top surface 160 may include a grid of touch-sensitive sensors and device 100 may include a processor that is configured to receive signals from the touch-sensitive sensors and determine whether the placement of the user's feet on the top surface is consistent with the suggested alignment. The device may also provide one or more of visual, audible or tactile feedback signals via an output component in communication with the processor (e.g., an LED light, speaker or haptic actuator) to indicate consistency with the suggested alignment (e.g., getting brighter, getting louder or increasing vibration as the alignment becomes more consistent).

When a user's foot is placed on the device in accordance with the suggested alignment, it may not be level nor orthogonal relative to the ground plane. For example and as show in FIG. 11, footprint 1150 outlines where a user's foot may contact left top surface 150 if a user's left foot was placed on the surface and centered in the forward direction as indicated by reference line 1115 (which may be, in at least some aspects, parallel to longitudinal axis 140). If left top surface 150 was generally planar and substantially level relative to the ground plane, the points of contact between the foot and left top surface 150 would be substantially level as well. However, since left top surface 150 itself is both tilted substantially 11.25° downward to the left and rotated substantially 22.5° counter-clockwise (relative to the ground plane), different points of contact would not be level with to each other or with respect to gravity when a user is standing on the device. Rather, as indicated by elevation reference lines 1101-04, point of contact 1111 (which corresponds with the inside of the ball of the foot) will be higher than point of contact 1112 (corresponding with the inside of the heel), which in turn will be higher than point of contact 1113 (corresponding with the outside of the ball of the foot), which in turn will be higher than point of contact 1114 (corresponding with the outside of the heel).

FIGS. 12-14 provide another illustration of the varying height of a single foot that is aligned with the top surface of the device as suggested above. All of the figures provide a perspective view of three rectangular reference planes, namely ground plane 1210, top surface plane 1220 and alignment plane 1230, relative to the three-dimensional Cartesian coordinate system represented by axes 1205. The perspective shown in the figure is subject to foreshortening, i.e., the greater the distance from the point of the view of the observer, the smaller the relevant element will appear in the figures. Ground plane 1210 may be a plane that is orthogonal to the direction of gravity.

Top surface plane 1220 may be a plane upon which a user's foot effectively rests when the user is using the device. As shown in FIG. 13, the device may be configured and arranged to orient top surface plane 1220 at a first angle 1260 relative to ground plane 1210. The first angle may fall within a first range of angle values. By way of example, the first range of values may be 11.25° plus or minus 0.25° such that first range may from 11° to 11.5°. In another example, the first range of values may be 11.25° plus or minus 1.25° such that first range may be from 10° to 12.5°. In yet another example, the first range of values may be 11.25° plus or minus 3.25° such that the range may be from 8° to 14.5°.

If the device is expected to be used on a flat, level floor (e.g., a floor that is that is substantially orthogonal to direction of gravity), the top and bottom surfaces of the device's housing may be substantially planar and fixed at an angle relative to each other in a manner similar to that described above in connection with device 100. However, other devices in accordance with the technology disclosed herein may be configured for use on surfaces that are not flat or level. For instance, the housing of another device in accordance with the technology disclosed herein may include a bottom portion that includes three or more legs that can be telescoped and moved to rest on an uneven floor or other ground surface. The top portion of such a device may have a substantially planar surface, e.g., it may be planar with respect to the points at which the foot contacts the top surface such that the device substantially establishes the plantar plane of the foot defined by its skeletal structure relative to direction of gravity. The top portion may be moveable relative to the bottom portion's points of contact with the ground surface. By way of example, such a device may have a middle portion disposed between the top and bottom portion that includes a gimbal for automatically stabilizing the top surface of the device, and thus the plane of the foot, relative to gravity even if the ground surface at which the device is used is uneven.

The intersection of the top surface plane and the ground plane may be used to define the relevant axes of a three-dimensional Cartesian coordinate system. For example and as represented by axes 1205, the x-y plane may be defined as being co-planar with the ground plane, the y-axis may be defined as being co-linear with the intersection line of top surface plane 1220 and ground plane 1210, and the y-z plane may be defined as a plane that is orthogonal to the ground plane and contains the intersection line of top surface plane 1220 and ground plane 1210. FIG. 13 and shows the planes from a line of sight co-linear with the x-y plane (ground plane 1210) and parallel with the y-axis, and FIG. 13 shows the planes from a line of sight looking directly downward at that plane, parallel with the z-axis.

Alignment plane 1230 may be a plane that is used to determine the suggested alignment of a person's foot relative to the ground plane. The alignment plane may be defined as a plane that is orthogonal to the ground plane and disposed at an angle relative to another reference plane that is orthogonal to the ground plane but contains the intersection of top surface plane with the ground plane. For example, such a reference plane may be y-z plane shown in FIGS. 12-14. In that regard and as shown in FIG. 14, alignment plane 1230 may be disposed at a second angle 1270 relative to the y-z plane. The second angle may fall within a second range of angle values. By way of example, the second range of values may be 22.5° plus or minus 0.5° such that the second range may be from 22° to 23°. In another example, the second range of values may be 22.5° plus or minus 2.5° such that the second range may be from 20° to 25°. In another example, the second range of values may be 22.5° plus or minus 5° such that the range of values may be between 17.5° and 27.5°.

Alignment line 1250, which is shown FIGS. 12-14 as a dark thick line, is defined as the line at which alignment plane 1230 intersects top surface plane 1220. When the first angle is within the first range and the second angle is within the second range, alignment line 1250 will be disposed at an angle relative to the ground plane. To help illustrate this effect, FIG. 12 includes elevation lines 1235 (dotted lines) that are contained in alignment plane 1230 and parallel to ground plane 1210.

Alignment line 1250 may be used to align a user's foot relative to the top surface. For the purposes of this disclosure, the longitudinal axis of a person's foot is considered to be the center line of the foot. When a user rests a foot on the top surface of the device such that the longitudinal axis of the user's foot is parallel to alignment line (e.g., directly above and parallel to alignment line 1250), the alignment of a user's foot may be similar to the suggested alignment described above in connection with FIG. 11.

During operation, a user may perform, on the device, many of the same exercises that are traditionally performed on the floor. By way of example, when operating device 100, a user may use the device by placing his or her left foot on left top surface 150 and right top surface 160, with his or her feet facing in the forward direction, and then perform exercises such as squats (with or without weights), kettlebell swings and lifts, dead lifts, overhead pressing, swinging clubs and ropes, plyometric jumps and physical practices such as standing meditation and standing breathing exercises.

Although the technology is not limited to particular dimensions or shapes, the outer shape of the device shown in FIGS. 1-9 is considered advantageous because, among other reasons, it also functions as visual indicia of the suggested alignment. For example, when viewed from the top down by a user standing on the device, top center edge 750 and left outer edge 754 are parallel to the direction of the left foot when it is in the suggested alignment, and top edge 752 and top edge 756 are perpendicular to that alignment. The other top edges, namely top edges 751, 753, 755 and 757, correspond with the substantially 22.5° rotation and may help a user get a better understanding of the direction of the tilt of the left and right portions when getting on or off the device.

By way of further example, the following edges shown in FIGS. 6-9 and their corresponding edges on right portion 120 may have the following approximate lengths when device 100 is sized for use by adults:

| | |
|---|---|
| top edge 750 | 332 mm |
| top edge 751 | 216 mm |
| top edge 752 | 169 mm |
| top edge 753 | 220 mm |
| top edge 754 | 230 mm |
| top edge 755 | 324 mm |
| top edge 756 | 130 mm |
| top edge 757 | 216 mm |
| side edge 760 | 132 mm |
| side edge 761 | 132 mm |
| side edge 762 | 93 mm |
| side edge 763 | 40 mm |
| side edge 764 | 18 mm |
| side edge 765 | 18 mm |
| side edge 766 | 47 mm |
| side edge 767 | 100 mm |
| bottom edge 770 | 330 mm |
| bottom edge 771 | 216 mm |
| bottom edge 772 | 165 mm |
| bottom edge 773 | 213 mm |
| bottom edge 774 | 229 mm |
| bottom edge 775 | 324 mm |
| bottom edge 776 | 127 mm |
| bottom edge 777 | 209 mm |

By way of another example, the following edges shown in FIGS. 6-9 and their corresponding edges on right portion 120 may have the following approximate lengths when device 100 is sized for use by adults:

| | |
|---|---|
| top edge 750 | 331 mm |
| top edge 751 | 216 mm |
| top edge 752 | 168 mm |
| top edge 753 | 217 mm |
| top edge 754 | 229 mm |
| top edge 755 | 324 mm |
| top edge 756 | 129 mm |
| top edge 757 | 214 mm |
| side edge 760 | 108 mm |
| side edge 761 | 108 mm |
| side edge 762 | 78 mm |
| side edge 763 | 35 mm |
| side edge 764 | 18 mm |
| side edge 765 | 18 mm |
| side edge 766 | 41 mm |
| side edge 767 | 83 mm |
| bottom edge 770 | 331 mm |
| bottom edge 771 | 216 mm |
| bottom edge 772 | 168 mm |
| bottom edge 773 | 217 mm |
| bottom edge 774 | 228 mm |
| bottom edge 775 | 324 mm |
| bottom edge 776 | 127 mm |
| bottom edge 777 | 209 mm |

As shown in FIG. 8, the height 810 of device 100 may be 132 mm, the width 820 of device 100 may be 444.50 mm, and the length of device in the y-direction (not shown) may be 609.60 mm.

The device may be composed of various materials. By way of example, the housing of device 100 may be manufactured via rotational molding using plastic polymers or constructed of wood, high density foam, cork, metal or combinations of the foregoing.

The top surface may be composed of a different material than the remainder of the device. For instance, in order to mitigate the likelihood of a user slipping on the device, left top surface 150 and right top surface 160 may each have a sturdy lower layer and a resilient upper layer of a material with a high coefficient of friction, such as rubber. The upper layer of the top surface of the device may also be texturized with knurls or similar protrusions to further mitigate the likelihood of slipping. Visual indicia 115 and 125 may be constructed of foam, rubberized material, grip tape, paint, decals or combinations of the foregoing.

The device may be configured so that the left portion and right portions can be moved with respect to each other. For example, FIG. 15 shows a device 1500 that is similar to the device 100. However, device 1500 includes a hinge 1580 that connects left portion 1510 to right portion 1516 and permits the two portions to be rotated towards or away from each other parallel to the ground plane. The device may also include indicia for indicating the relative rotation of the tilt. By way of further example, device 1500 may include angle indicator 1590, and left portion 1510 may include a plurality of lines that are labeled with angle numbers and meet at hinge 1580. Right portion 1516 may include a similar plurality of lines that mirrors the angle indicator on left portion 1510. The approximate angle of tilt relative to the forward direction of the device may correspond with the two lines of the angle indicator that line up the most closely with each other. In the example shown in FIG. 15, the two lines labelled "45°" are relatively co-linear with each and, as shown by axes 1501 and 1502, the angle of tilt of left top surface 1550 and right top surface 1560 with respect to longitudinal axis 1540 is 45° and −45° respectively. Other angle indicia may also be used. For instance, instead of indicating the relative angle of tilt relative to the device's longitudinal axis, the angle indicator may indicate other angles such as the angle between the direction of left foot indicia 1515 and right visual indicia 1525.

The device may also be configured to permit the left and right portion to be detached from each other. For example and as shown in FIG. 16, hinge 1580 may also permit left portion 1510 to be detached from right portion 1516, in which case a user may space the portions further from one another and use device 1500 as previously described in connection with device 100.

Another example of the left and right portion being separated from each other is shown in FIG. 17, which illustrates top-down view of a pair of shoes 1700 in accordance with the technology disclosed herein. The left portion is associated with left shoe 1710 and the right portion is associated with right shoe 1720. In that regard, left top surface 1750 of the sole of left shoe 1710 may be tilted substantially 11.25° downward to the left and rotated substantially 22.5° counter-clockwise and right top surface 1760 of the sole of right shoe 1720 may be tilted substantially 11.25° downward to the right and rotated substantially 22.5° clockwise. The indicia for the proper foot alignment may be omitted from pair of shoes 1700 since a properly-fitted shoe may automatically align the left foot's longitudinal axis 1715 and right foot's longitudinal axis 1716 relative to the direction of tilt and rotation.

The top surfaces of the soles of the pair of shoes shown in FIG. 15, as well as the top surface of other devices in accordance with the technology disclosed herein, may be non-planar. For instance, left top surface 1550 of left shoe 1710 and right top surface 1760 of right shoe 1720 may include cushioned arches that extend upwards relative to the rest of the sole to provide additional comfort or support to the user's foot. Yet further, even if the portion of the top surface upon which a user stands is planar, the remainder of the top surface the top surface of device 100 may be curved. For example, while top center edge 750 of device 100 is shown in FIG. 1 as a linear edge, the center of device 100, left top surface 150 and right top surface 160 may collectively form a smooth single surface that gently curves and transitions from the tilt and rotation of left portion 110 to the tilt and rotation of right portion 120. In that regard, the topography of the top surface(s) of the device may be non-planar, provided the surface(s) align the left foot, the right foot or both within the disclosed angle range.

A device in accordance with the technology described herein may include other features as well. For instance, FIG. 18 illustrates the bottom of a device 1800 with a shape similar to that of device 100. Device 1800 includes handles 1880 and 1890 that are integral with left portion 1810 and right portion 1818, respectively. The bottom surface may also include feet, such as rubberized foot 1891, to help keep the device in place while being used. For example and as show in FIG. 18, the bottom surface of left portion 1810 and the bottom surface of right portion 1818 may each include four rubberized feet at opposite corners of each portion.

Figure 19:
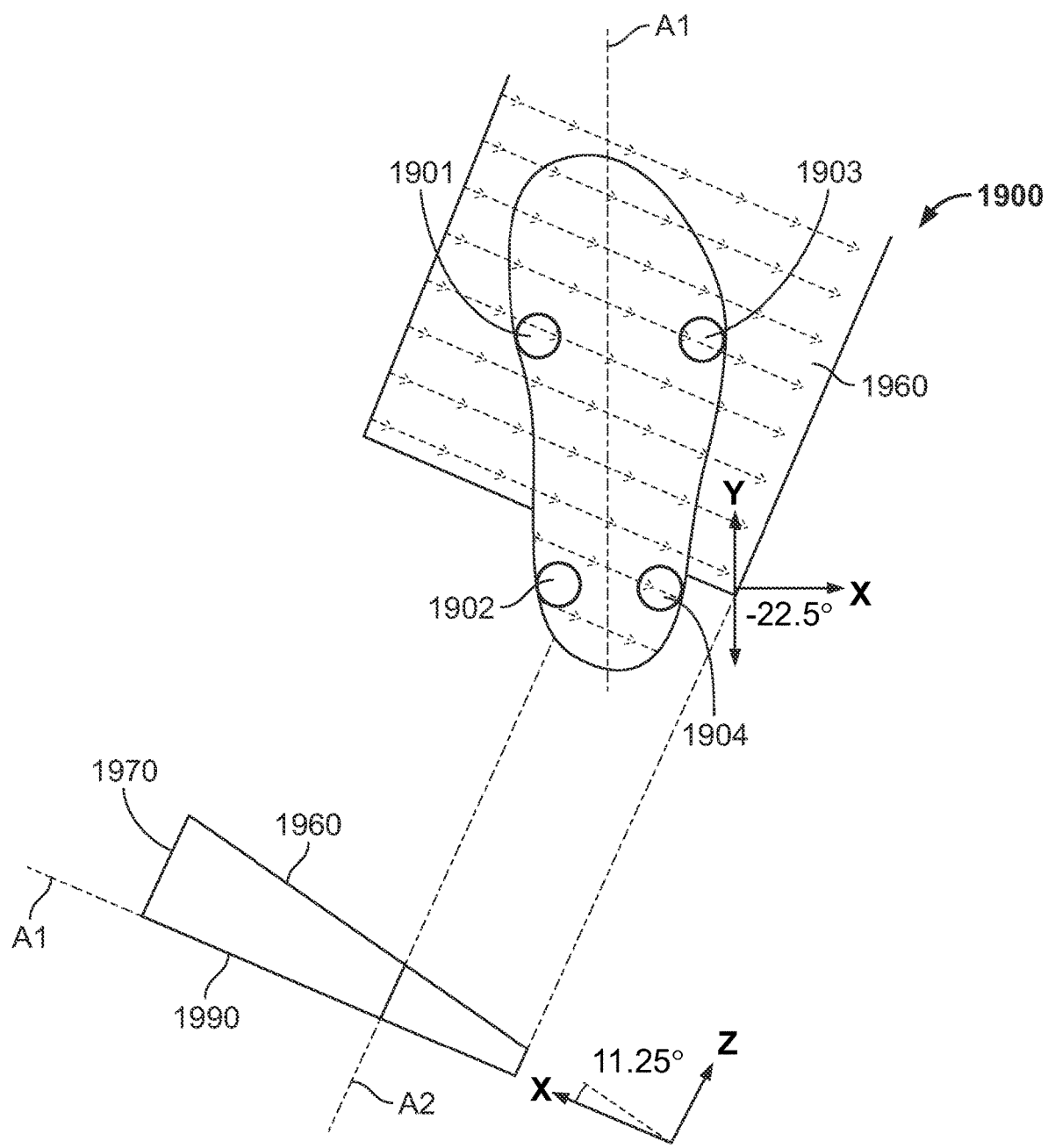
FIG. 19 is a top-down view showing four different locations of contact of a foot of a user on an example device.

FIG. 19 is a top-down view showing four different locations of contact of a foot of a user on an example device or postural platform 1900. A top surface 1960 is oriented at a complex angle with respect to bottom surface 1990. Top surface 1960 is tilted or rotated about a first rotational axis A1 parallel to a bottom surface 1990 between 8° and 14.5°. In the present example, top surface is rotated about the first rotational axis 11.25°. Given that device 1900 in the present example is a right postural platform, top surface 1960 is titled downward to the right. Top surface 1960 is also rotated or turned clockwise about a second rotational axis A2 perpendicular to the bottom surface 1990 between 17.5° and 27.5°. In the present example, top surface is rotated about the second rotational axis 22.5°. A perimeter side wall 1970 is located between top surface 1960 and bottom surface 1990. While the top portion of FIG. 19 is shown in a top view the bottom portion of FIG. 19 is a side view rotated 90° from the top view. These top and side views together provide perspective as to where the foot of a user is preferably located on the top surface of the present postural platform.

When a user places his or her right foot on top surface 1960 of postural platform 1900, different points of contact of the foot are no longer level with respect to each other. For example, a first point of contact 1901 corresponding to the inside of the ball of the foot adjacent the first metatarsal will be higher with respect to the ground or reference plane in a linear direction perpendicular to the reference plane than a second point of contact 1902 corresponding with the inside of the heel, which in turn will be higher than a third point of contact 1903 corresponding with the outside of the ball of the foot, which in turn will be higher than a fourth point of contact 1904 corresponding with the outside of the heel.

Figure 20B:
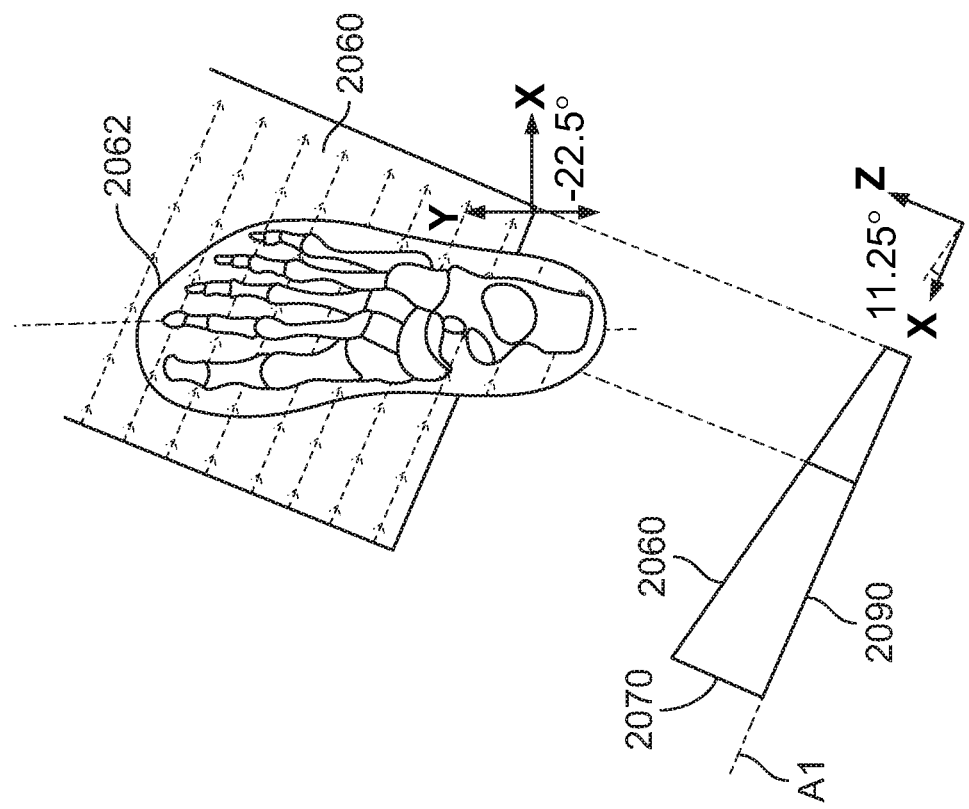
FIG. 20B is a top-down view of FIG. 20A without the talus bone of the exemplary right foot and ankle being present.
Figure 20A:
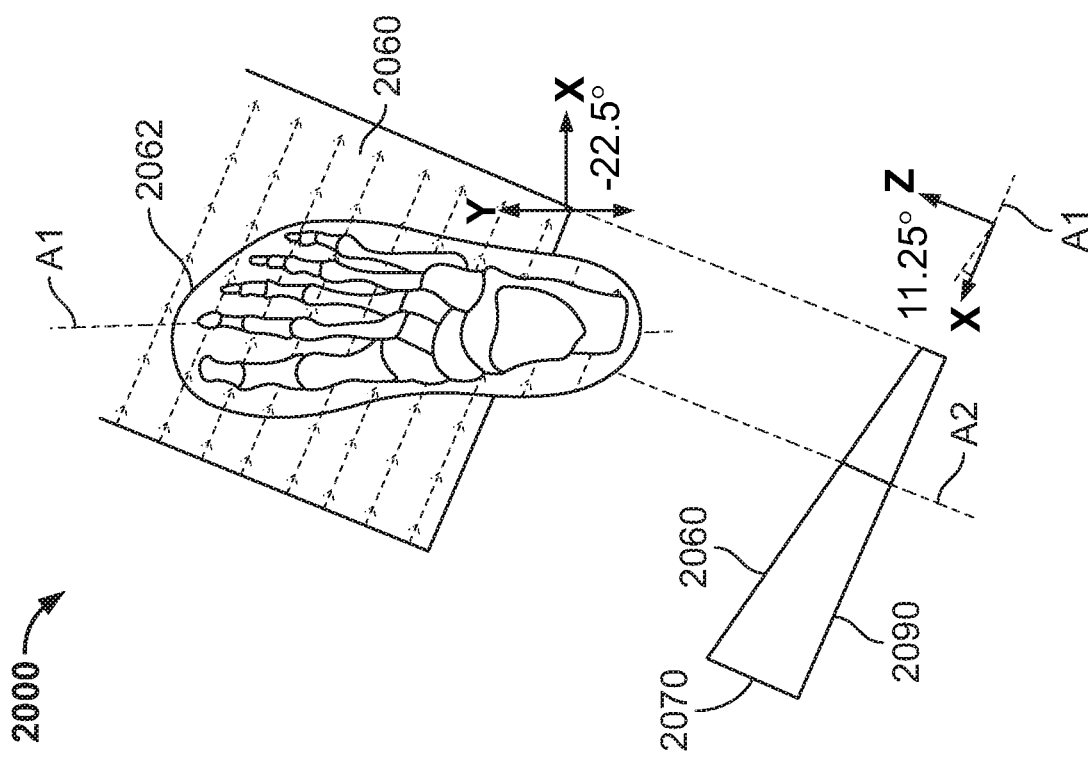
FIG. 20A is a top-down view showing an orientation of each of the bones of an exemplary right foot and ankle of a user superimposed on an outline of the bones of a right foot with respect to an example device.

FIG. 20A shows an orientation of each of the bones of an exemplary right foot and ankle with respect to a postural platform 2000 having a planar top surface 2060 and a planar bottom surface 2090. In this aspect, the top surface 2060 is shown having an alternative periphery 2062 that surrounds the bones of the right foot. In this aspect, the perimeter of a right shoe is shown in a similar manner to the right shoe shown in FIG. 17. In the present figure, however, the right shoe is superimposed on a larger square shaped depiction of a top surface 2060 in order to show the orientation of the top surface 2060 with respect to the bottom surface 2090 in more detail.

Bottom surface 2090 defines a first longitudinal axis A1 which is parallel to bottom surface 2090 and is parallel to the y-axis. Top surface 2060 or top surface periphery 2062 is rotated about longitudinal axis A1 or tilted downwardly to the right substantially 11.25°. In other embodiments, top surface 2060 or top surface periphery 2062 may be rotated about longitudinal axis A1 or tilted downwardly to the right more or less than 11.25°. Bottom surface 2090 further defines a second longitudinal axis A2 parallel to the z-axis and perpendicular to the first longitudinal axis A1. Top surface 2060 or top surface periphery 2062 is rotated about second longitudinal axis A2 or turned clockwise with respect to the second longitudinal axis 22.5°. In other embodiments, top surface 2060 or top surface periphery 2062 may be rotated about second longitudinal axis or turned clockwise with respect to the second longitudinal axis A2 more or less than 22.5°. The direction of the arrows in this figure depicts the orientation of top surface 2060 and top surface periphery 2062 with respect to bottom surface 2090 angled in both the y and z axes.

When a person is in an upright standing position, the natural weight bearing forces are toward the inside or medial portion of the body. For each foot, the weight of the body is generally distributed to the big toe toward the inside of the body. The top surface 2060 or top surface periphery 2062 of postural platform 2000 is oriented to transfer the weight laterally or to the outside where the skeleton is more substantial.

FIG. 20B shows the talus bone being removed. The talus lies posteriorly between the lower limb bones above, the calcaneum below and the other tarsal bones in front. It has no muscle attachments but is important for transmitting the body weight from the tibia down to the calcaneum and forwards to the navicular and other tarsal bones. It therefore is a floating bone that acts as a wedge between the tibia to bones of the foot. The talus has the articulating facets with the calcaneus, delineated as the anterior, middle and posterior facets. These facets distribute weight in such a manner that can lead to the collapse of the bones of the foot or rotation of the foot bones medially or toward the inside of the body. A benefit of using a performance or postural platform for standing, walking and/or training, is shifting this normal weight distribution laterally in turn leading to greater balance, performance and strength of the ankle and foot bones as well as reducing the potential wear and tear on these bones.

Figure 20C:
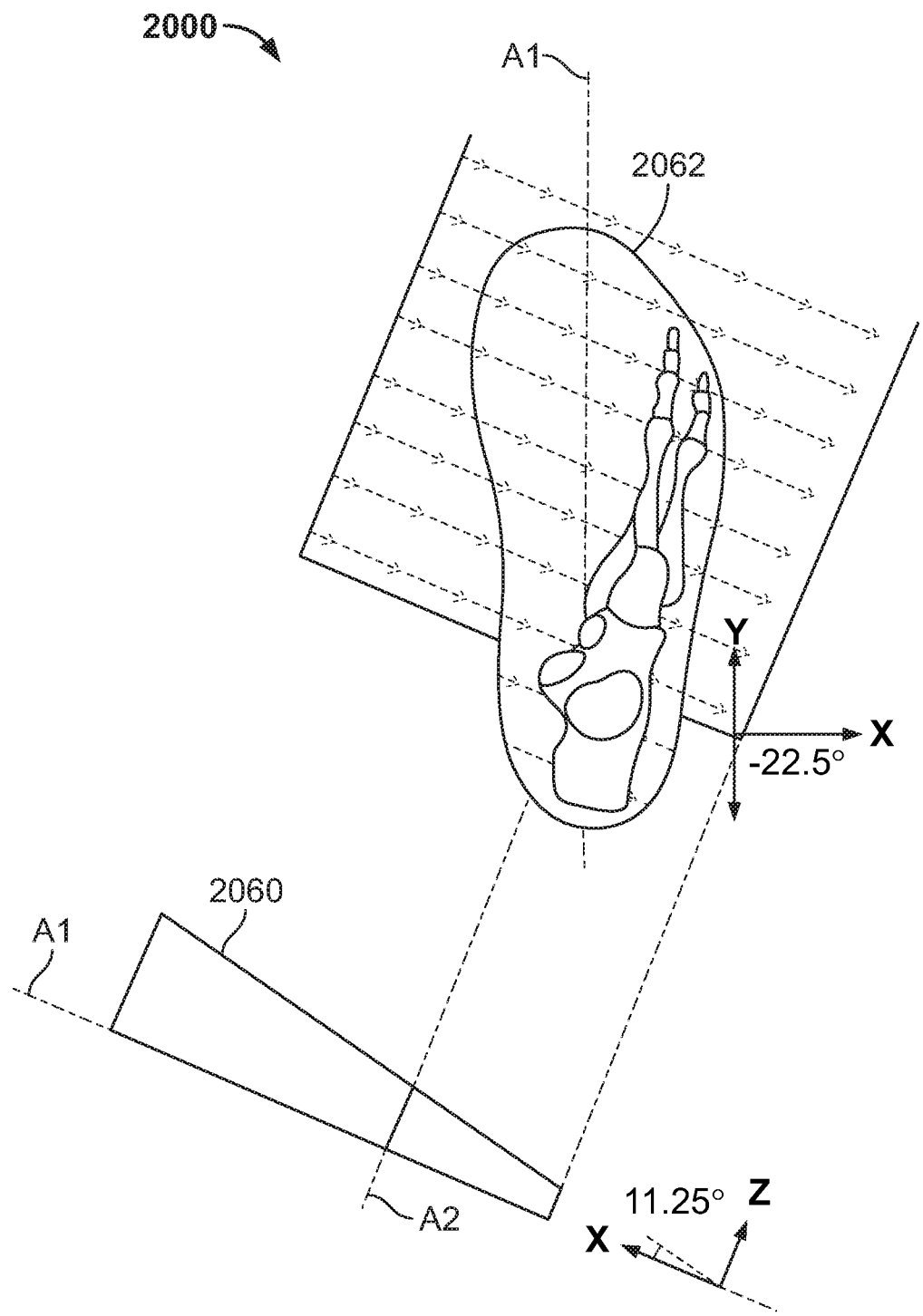
FIG. 20C is a top-down view of FIG. 20A showing the fourth and fifth metatarsals and cuboid without the first, second, third metatarsals and respective medial, intermediate and lateral cuneiforms being present.

FIG. 20C shows the fourth and fifth metatarsals and cuboid without the first, second, third metatarsals and respective medial, intermediate and lateral cuneiforms being present. Here, body weight is distributed to the base of the skeleton which may be referred to as the heel bone and fourth and fifth metatarsals when standing on postural platform 2000. The orientation of top surface 2060 and top periphery surface 2062 of postural platform 2000 reorients the facets of the talus with respect to the calcaneus and other bones of the feet, which redistributes the body weight of a user to the outside bones of the foot where the skeleton is structurally strong.

Figure 21A:
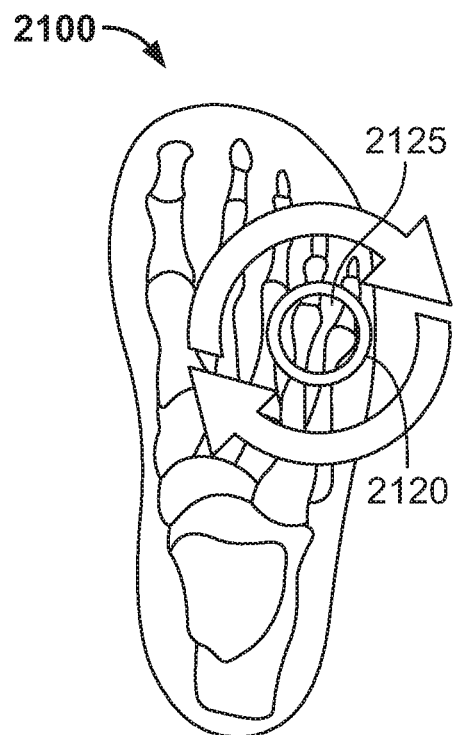
FIG. 21A is a top-down view showing exemplary right foot and ankle bones with respect to an example device and a pivot point intermediate the fourth and fifth metatarsals.
Figure 21B:
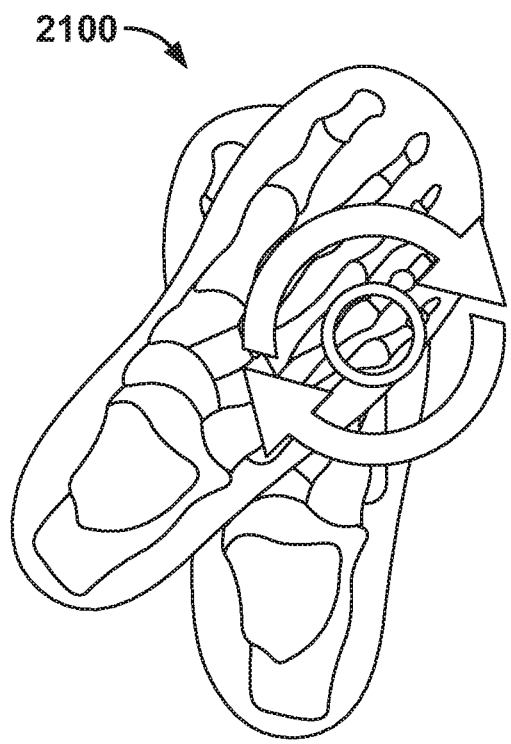
FIG. 21B is a top down view of FIG. 21A superimposed on another view of FIG. 21A and rotated clockwise about the pivot point.
Figure 22:
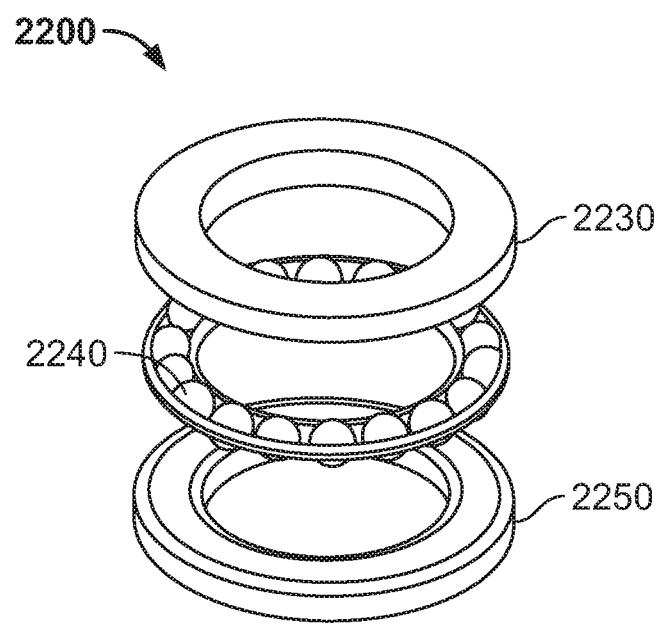
FIG. 22 an exemplary bearing system that is configured to contact a bottom surface of an example device such that the example device can rotate about the respective pivot points shown in FIGS. 21A and 21B.
Figure 23A:
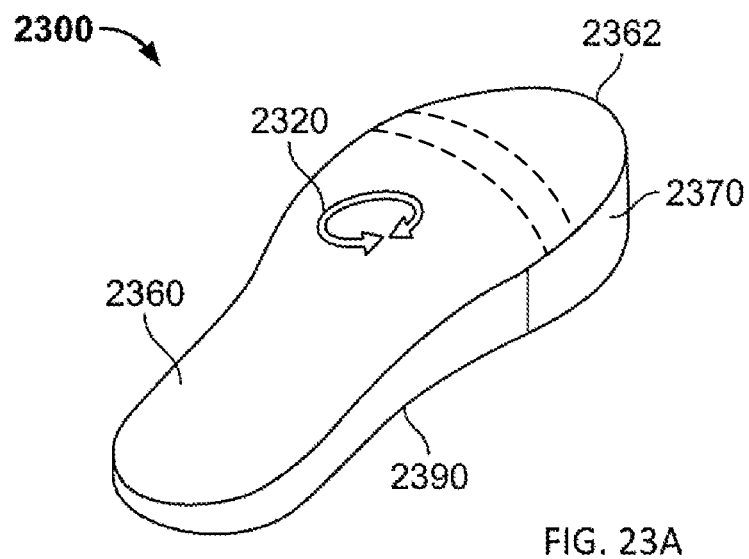
FIG. 23A is a perspective view of an example device for a left foot showing a pivot location on the top surface thereof.
Figure 23B:
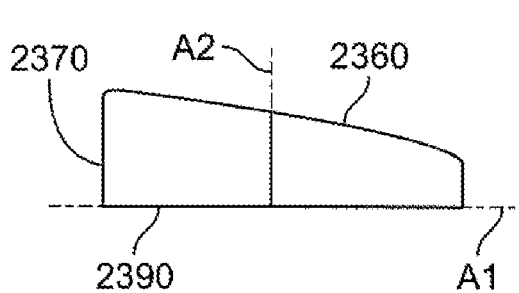
FIG. 23B is a front view of the example device of FIG. 23A.
Figure 23C:
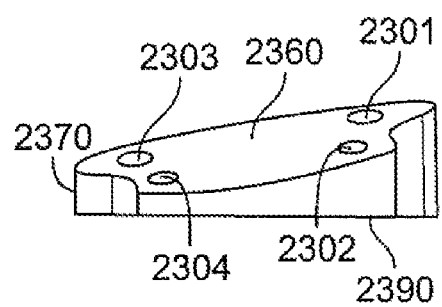
FIG. 23C is a rear view of the example device of FIG. 23A.
Figure 23D:
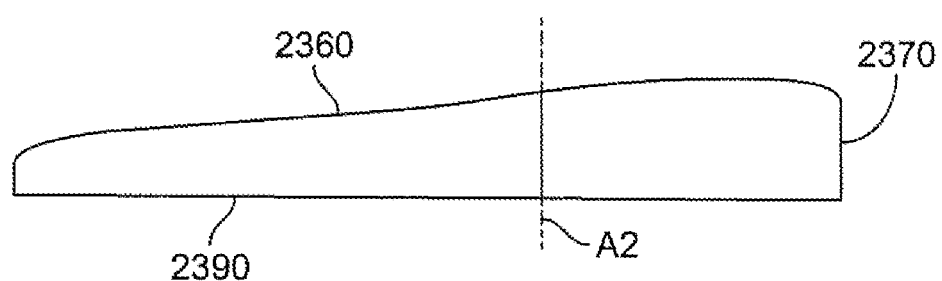
FIG. 23D is a right side view of the example device of FIG. 23A.
Figure 23E:
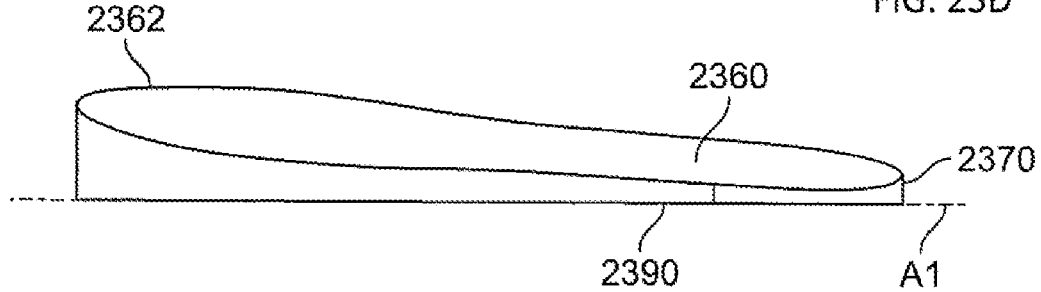
FIG. 23E is a left side view of the example device of FIG. 23A.

FIG. 21A shows exemplary right foot and ankle bones with respect to a postural platform 2100 in which a pivot location 2110 is depicted. The pivot location 2120 has a pivot axis depicted by point 2125 located between the fourth and fifth metatarsal bones. The arrows depict rotation of postural platform in a clockwise direction about pivot point 2125. An exemplary pivot member 2200 when coupled to postural platform 2100 allows postural platform 2100 to pivot from a neutral or first position as shown in FIG. 20A to an active or second position as shown in FIG. 21B. While the arrows are only depicted in a clockwise direction, it should be understood that the rotational movement of a right postural platform 2100 from the neutral position shown in FIG. 21A to a rotated clockwise position about pivot point 2125 shown in FIG. 21B, is limited by the external rotation capabilities of a particular user. Pivot member 2200 allows postural platform 2100 to then rotate counterclockwise back to the neutral position shown in FIG. 21A. When rotating back to the neutral position this is limited by the internal rotation capabilities of the user. Pivot member 2200 therefore allows a user to alternate between internal and external rotational movements of postural platform 2200 during strength training, for example. As shown in FIG. 22, pivot member 2200 is an exemplary bearing system that is configured to contact a bottom surface of postural platform. Pivot member 2200 has a top plate 2230 that is fixedly coupled to a bottom surface of a postural platform and a bottom plate 2250 that rotates with respect to top plate 2230 along the second rotational axis of postural platform. Top plate 2230 and bottom plate 2250 may rotate with respect to each other via a plurality of rotatable ball bearings 2240 housed in between top plate 2230 and bottom plate 2250. The general concept of the incorporation of a pivot system to a postural platform is to allow a postural platform to rotate in alternating clockwise and counterclockwise directions in order to strengthen the muscles and joints, for example, of the foot and ankle to facilitate strength training and weight distribution of the body laterally. In other embodiments, any device that allows the postural platform to pivot during use can be implemented. FIGS. 23A-E show an example device or postural platform 2300 for a left foot. FIG. 23 is a perspective view showing a pivot location 2320 on top surface 2360 if a pivot member such as pivot member 2200 shown in FIG. 22 was fixedly coupled to a bottom surface 2390 of platform 2300. Platform 2300 includes a perimeter side wall 2370 between top surface 2360 and bottom surface 2390. In this embodiment top surface 2360 includes a periphery 2362 that has the general shape of a left foot. A covering (not shown) for housing the foot of a user in contact with top surface 2360 can be coupled to the entirety of periphery 2362 or adjacent the entirety of periphery 2362. In other embodiments, a covering (as depicted by dotted lines in FIG. 23A) can be coupled to a portion of periphery 2362 or adjacent a portion of periphery 2362. As can be seen in each of FIGS. 23A-E, the height of perimeter side wall 2370 varies about the perimeter of platform 2300. For example, the height of perimeter side wall 2370 in an anterior or front portion of platform 2370 as seen in FIG. 23B in which the toes of a user would be located is generally more than the height of perimeter side wall 2370 in a back portion of platform 2370 as seen in FIG. 23C in which the heal of the user would be located. The height of perimeter side wall 2370 in a medial or right portion of platform 2370 as seen in FIG. 23D generally decreases from an anterior or front of the foot where the toes are located to a posterior or rear of the foot where the heal is located. The height of perimeter side wall 2370 in a lateral or left portion of platform 2370 as seen in FIG. 23E generally decreases from an anterior or front of the foot where the toes are located to a posterior or rear of the foot where the heal is located.

As shown for example in FIG. 23C, when a user places his or her left foot on top surface 2360 of postural platform 2300, different points of contact of the foot are no longer level with respect to each other. For example, a first point of contact 2301 corresponding to the inside of the ball of the foot adjacent the first metatarsal will be higher with respect to the ground or reference plane in a linear direction perpendicular to the reference plane than a second point of contact 2302 corresponding with the inside of the heel, which in turn will be higher than a third point of contact 2303 corresponding with the outside of the ball of the foot, which in turn will be higher than a fourth point of contact 2304 corresponding with the outside of the heel.

In the above embodiments, the example devices and postural platforms are shown with a planar top surface. In other embodiments, the top surface substantially conforms to the shape of the foot of the user when the foot of the user is in contact with the top surface. In other embodiments, the top surface has the general shape or contour of the foot of a user without the foot of a user being in contact with the top surface. The top surface may conform to the contours of a foot of a user in that it is not completely rigid. In these embodiments, the top surface may compress such that the portion of the top surface in contact with the foot of the user takes the general shape of the contours of the bottom surface of the user's foot. While the top surface may compress, this does not alter the relative orientation of the top surface as defined by the first, second, third and fourth contact points, for example. It is further appreciated that postural platforms may be an insert or wedge for insertion in a sandal, shoe, sneaker, boot or any foot covering or the general non-removable foot contact support within a sandal, shoe, sneaker, boot or any foot covering.

As these and other variations and combinations of the features discussed above can be utilized without departing from the invention as defined by the claims, the foregoing description of the embodiments should be taken by way of illustration rather than by way of limitation of the invention as defined by the claims. The provision of examples of the invention (as well as clauses phrased as "such as," "e.g.", "including" and the like) should not be interpreted as limiting the invention to the specific examples; rather, the examples are intended to illustrate only some of many possible aspects. Similarly, references to "based on" and the like means "based at least in part on".

The invention claimed is:

1. A postural platform configured to redistribute weight of a user in a standing position comprising:
    a top plane and a reference plane;
    the top plane being parallel to the reference plane in an initial orientation, the top plane and the reference plane forming a second orientation by tilting the top plane to a first degree about a first axis parallel to the reference plane and then rotating the top plane to a second degree about a second axis orthogonal to the reference plane, wherein the second degree is greater than the first degree;
    a top surface being parallel to the top plane in the second orientation, the top surface configured as a contact surface for a foot of the user;
    a bottom surface being parallel to the reference plane in the second orientation, such that the top surface has a fixed orientation relative to the bottom surface based on the second orientation of the top plane relative to the reference plane; and
    a perimeter side surface between the top and bottom surfaces,
    wherein the postural platform is configured such that when the foot of the user is in contact with the top surface, a first point of contact on the top surface corresponding to an inside of a ball of the foot is higher with respect to the reference plane than a second point of contact corresponding with an inside of a heel of the foot, the second point of contact being higher with respect to the reference plane than a third point of contact corresponding with an outside of the ball of the foot, the third point of contact being higher with respect to the reference plane than a fourth point of contact corresponding with an outside of the heel of the foot.

2. The postural platform of claim 1, further comprising a pivot member coupled to the bottom surface of the postural platform.

3. The postural platform of claim 2, wherein the pivot member is configured to allow the top surface to rotate about the second axis.

4. The postural platform of claim 2, wherein the pivot member has a top plate that is fixedly coupled to the bottom surface of the postural platform and a bottom plate that rotates with respect to the top plate along the second axis.

5. The postural platform of claim 1, wherein the top plane in the second orientation is tilted the first degree between 10° and 12.5° about the first axis.

6. The postural platform of claim 5, wherein the top plane in the second orientation is rotated the second degree between 20° and 25° about the second axis.

7. A postural platform system comprising a left and a right postural platform according to claim 1, wherein the left and the right postural platforms are minor images of one another and are configured to support a left and a right foot of the user, respectively.

8. The postural platform system of claim 7, wherein each of the left and right postural platforms have a covering coupled to at least a portion of a perimeter of the respective top surfaces of each of the left and right postural platforms for forming at least a partial housing configured to receive the respective left and right feet of the user when located between the respective top surfaces and coverings.

9. The postural platform of claim 1, wherein the top surface is configured to conform to a shape of the foot of the user.

10. The postural platform of claim 1, wherein the top surface is planar.

11. The postural platform of claim 1, wherein the top surface has an outer periphery shaped to match an outer periphery of the foot of the user.

12. The postural platform of claim 1, wherein the top surface includes visual indicia configured to define how the foot of the user is to be oriented relative to the top surface when the foot of the user is in contact with the top surface.

13. A postural platform configured to redistribute weight of a user in a standing position comprising:
    a top plane and a reference plane;
    the top plane being parallel to the reference plane in an initial orientation, the top plane and the reference plane forming a second orientation by tilting the top plane to a first degree about a first axis parallel to the reference plane and then rotating the top plane to a second degree about a second axis orthogonal to the reference plane, wherein the second degree is greater than the first degree;

a top surface being parallel to the top plane in the second orientation, the top surface configured as a contact surface for a foot of the user;

a bottom surface being parallel to the reference plane in the second orientation, such that the top surface is oriented at a fixed complex angle relative to the bottom surface based on the second orientation of the top plane relative to the reference plane, such that when the foot of the user is in contact with the top surface, a first point of contact on the top surface corresponding to an inside of a ball of the foot is higher with respect to the reference plane than a second point of contact corresponding with an inside of a heel of the foot, the second point of contact being higher with respect to the reference plane than a third point of contact corresponding with an outside of the ball of the foot, the third point of contact being higher with respect to the reference plane than a fourth point of contact corresponding with an outside of the heel of the foot;

a perimeter side surface between the top and bottom surfaces; and a covering coupled to at least a portion of a perimeter of the top surface for forming at least a partial housing configured to receive the foot of the user located between the top surface and covering.

14. The postural platform of claim 13, further comprising a pivot member coupled to the bottom surface of the postural platform, the pivot member configured to allow the contact surface to rotate about the second axis.

15. The postural platform of claim 14, wherein the pivot member has a top plate that is fixedly coupled to the bottom surface of the postural platform and a bottom plate that rotates with respect to the top plate along the second axis.

16. The postural platform of claim 13, wherein the top surface is planar.

17. The postural platform of claim 13, wherein the top surface is configured to conform to a natural shape of the foot of the user.

18. The postural platform of claim 13, wherein the complex angle between the top and bottom surfaces is defined by the top plane in the second orientation being tilted the first degree between 10° and 12.5° about the first axis and rotated the second degree between 20° and 25° about the second axis.

19. The postural platform of claim 13, wherein the top surface includes visual indicia configured to define how the foot of the user is to be oriented relative to the top surface when the foot of the user is in contact with the top surface.

* * * * *